(12) United States Patent
Stampfer et al.

(10) Patent No.: US 9,376,662 B2
(45) Date of Patent: *Jun. 28, 2016

(54) INCREASING CELL CULTURE POPULATION DOUBLINGS FOR LONG-TERM GROWTH OF FINITE LIFE SPAN HUMAN CELL CULTURES

(71) Applicant: The Regents of the University of California, Oakland, CA (US)

(72) Inventors: Martha R. Stampfer, Oakland, CA (US); James C. Garbe, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/627,888

(22) Filed: Feb. 20, 2015

(65) Prior Publication Data

US 2015/0247121 A1 Sep. 3, 2015

Related U.S. Application Data

(63) Continuation of application No. 12/242,474, filed on Sep. 30, 2008, now Pat. No. 8,962,325, which is a continuation of application No. PCT/US2007/065718, filed on Mar. 30, 2007.

(60) Provisional application No. 60/788,261, filed on Mar. 31, 2006.

(51) Int. Cl.
*C12N 5/00* (2006.01)
*C12N 5/071* (2010.01)

(52) U.S. Cl.
CPC .......... *C12N 5/0631* (2013.01); *C12N 2500/90* (2013.01); *C12N 2500/99* (2013.01); *C12N 2501/30* (2013.01); *C12N 2501/31* (2013.01); *C12N 2501/80* (2013.01)

(58) Field of Classification Search
None
See application file for complete search history.

(56) References Cited

U.S. PATENT DOCUMENTS

| | | | |
|---|---|---|---|
| 4,423,145 A | 12/1983 | Stampfer et al. | |
| 4,808,532 A * | 2/1989 | Stampfer | 435/371 |
| 6,692,961 B1 * | 2/2004 | Judd et al. | 435/406 |

OTHER PUBLICATIONS

Sapino et al. Endocrinology, 1993. vol. 133, No. 2, pp. 838-842.*
Ben-Porath, I. and Weinberg, R.A., "When cells get stressed: an integrative view of cellular senescence," The Journal of Clinical Investigation, vol. 113, No. 1, pp. 8-13 (2004).
Blasco, M.A., "Telomerase beyond telomeres," Nature Reviews 2:627-632 (2002).
Brenner et al., "Increased p16 expression with first senescence arrest in human mammary epithelial cells and extended growth capacity with p16 inactivation," Oncogene 17:199-205 (1998).
Cassoni et al., "Oxytocin and Oxytocin Receptors in Cancer Cells and Proliferation," Journal of Neuroendocrinology 16:362-364 (2004).
Gonzalez-Suarez et al., "Increased epidermal tumors and increased skin wound healing in transgenic mice overexpressing the catalytic subunit of telomerase, mTERT, in basal keratinocytes," European Molecular Biology Organization 20:2619-2630 (2001).
Hammond et al., "Serum-free growth of human mammary epithelia cells: Rapid clonal growth in defined medium and extended serial passage with pituitary extract," Proceedings of the National Academy of Sciences of the USA 81:5435-5439 (1984).
International Search Report for Application No. PCT/US07/65718, "Increasing Cell Culture Population Doublings for Long-Term Growth of Finite Life Span Human Cell Cultures," Mar. 6, 2008.
Jiang et al., "Telomerase expression in human somatic cells does not induce changes associated with a transformed phenotype," Nature Genetics 21:111-114 (1999).
Li et al., "Transcriptional changes associated with breast cancer occur as normal human mammary epithelial cells overcome senescence barriers and become immortalized," Molecular Cancer 6.7:1-17 (2007).
Lu et al., "Telomerase protects developing neurons against DNA damage-induced cell death," Developmental Brain Research 131:167-171 (2001).
Masutomi et al., "Telomerase Maintains Telomere Structure in Normal Human Cells," Cell 114:241-253 (2003).
Morales et al. ,"Absence of cancer-associated changes in human fibroblasts immortalized with telomerase," Nature Genetics 21:115-118 (1999).
Oh et al., "Telomerase reverse transcriptase promotes cardiac muscle cell proliferation, hypertrophy, and survival," Proceedings of the National Academy of Sciences of the USA 98:10308-11033 (2001).
Pavel et al., "Peripherally administered Angiotensin II AT1 receptor antagonists are anti-stress compounds in vivo," Annals of the New York Academy of Sciences 1148: 360-366 (2008).
Smith et al., "Telomerase modulates expression of growth-controlling genes and enhances cell proliferation," Nature Cell Biology 5:474-479 (2003).
Stampfer et al., "Expression of the telomerase catalytic subunit, hTERT, induces resistance to transforming growth factor β growth inhibition in p16INK4A(–) human mammary epithelial cells," Proceedings of the National Academy of Sciences of the USA 98:4498-4503 (2001).
Taylor-Papadimitriou et al., "Keratin expression in human mammary epithelial cells cultured from normal and malignant tissue: relation to in vivo phenotypes and influence of medium," Journal of Cell Science 94:403-413 (1989).

(Continued)

*Primary Examiner* — Celine Qian
(74) *Attorney, Agent, or Firm* — Bozicevic, Field & Francis LLP

(57) ABSTRACT

Cell culture media formulations for culturing human epithelial cells are herein described. Also described are methods of increasing population doublings in a cell culture of finite life span human epithelial cells and prolonging the life span of human cell cultures. Using the cell culture media disclosed alone and in combination with addition to the cell culture of a compound associated with anti-stress activity achieves extended growth of pre-stasis cells and increased population doublings and life span in human epithelial cell cultures.

20 Claims, 19 Drawing Sheets

(56) References Cited

OTHER PUBLICATIONS

Wei et al.,"Expression of Catalytically Active Telomerase Does Not Prevent Premature Senescence Caused by Overexpression of Oncogenic Ha-Ras in Normal Human Fibroblasts," Cancer Research 59:1539-1543 (1999).

Yano et al., "Long-term culture of adult murine epidermal keratinocytes," The British Journal of Dermatology 153:1101-1104 (2005).

Yaswen et al., "Molecular changes accompanying senescence and immortalization of cultured human mammary epithelial cells," The International Journal of Biochemistry and Cell Biology, vol. 34, pp. 1382-1394 (2002).

* cited by examiner

Fig.5
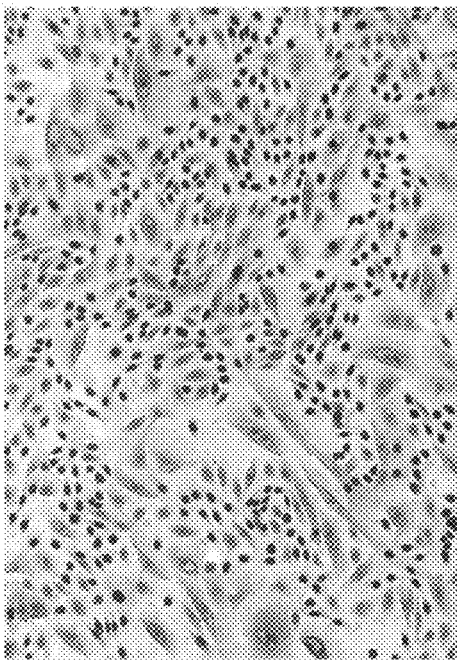
184◇ in M85+oxytocin at 11p
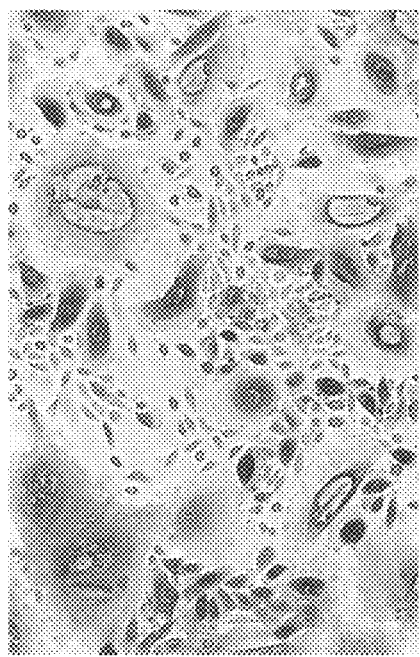
24 hr LI
p16 IHC
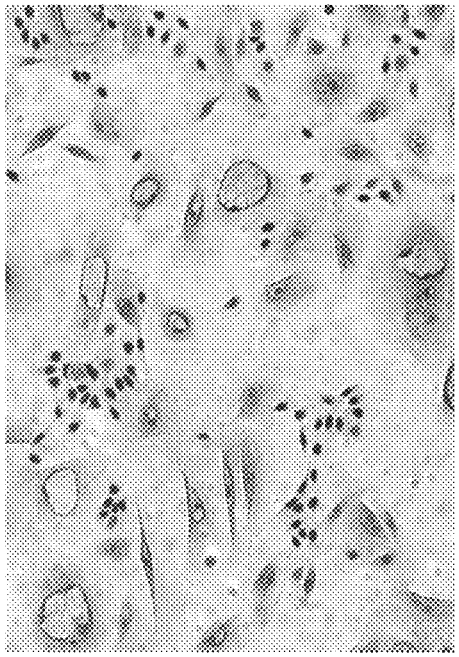
184◇ in M85 at 9p Fig. 12
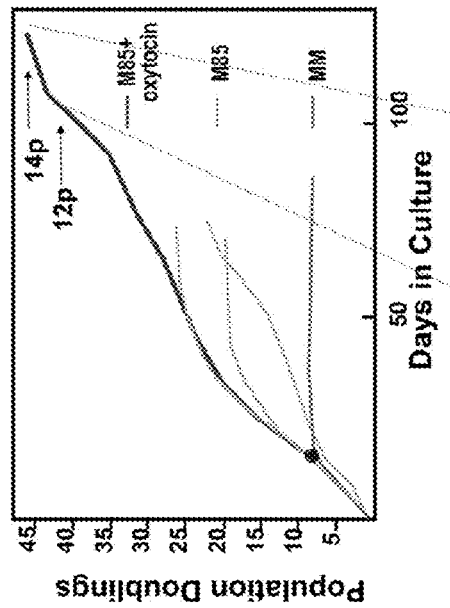
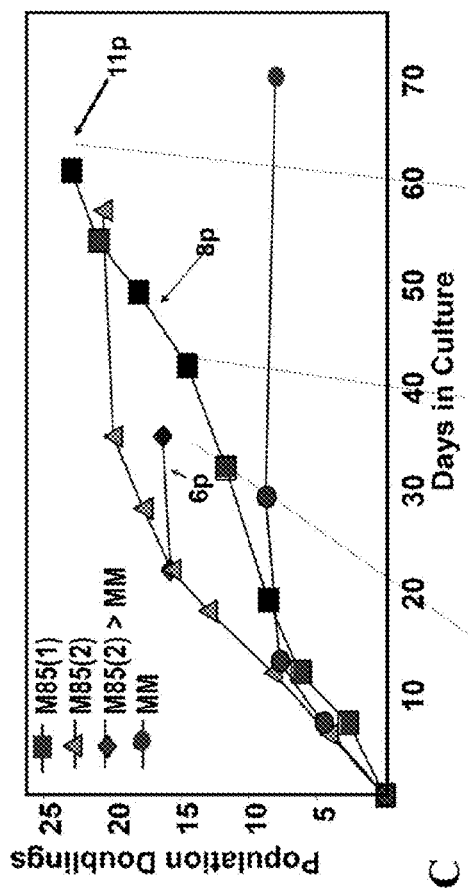
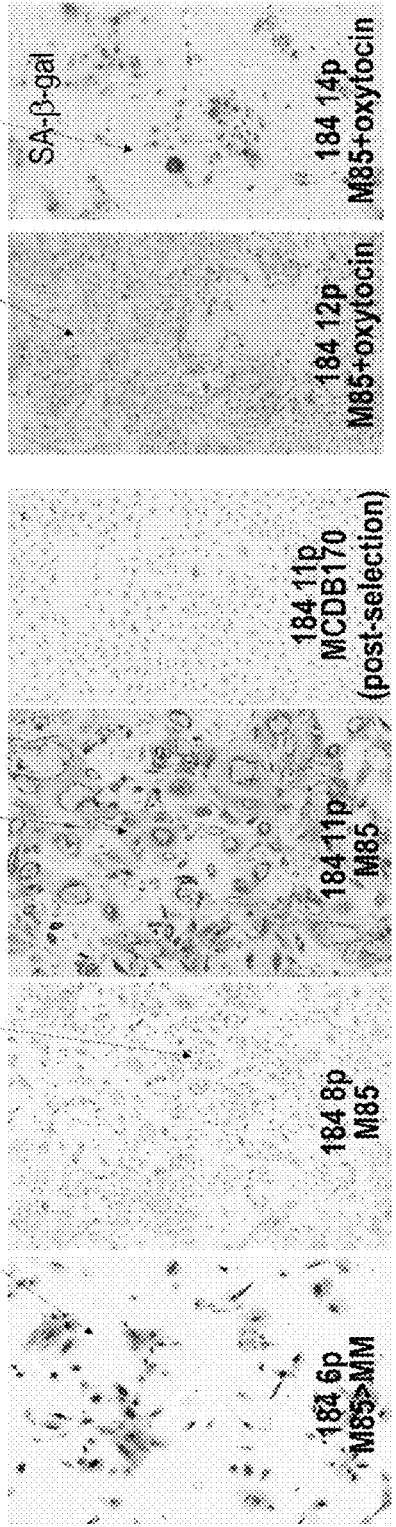

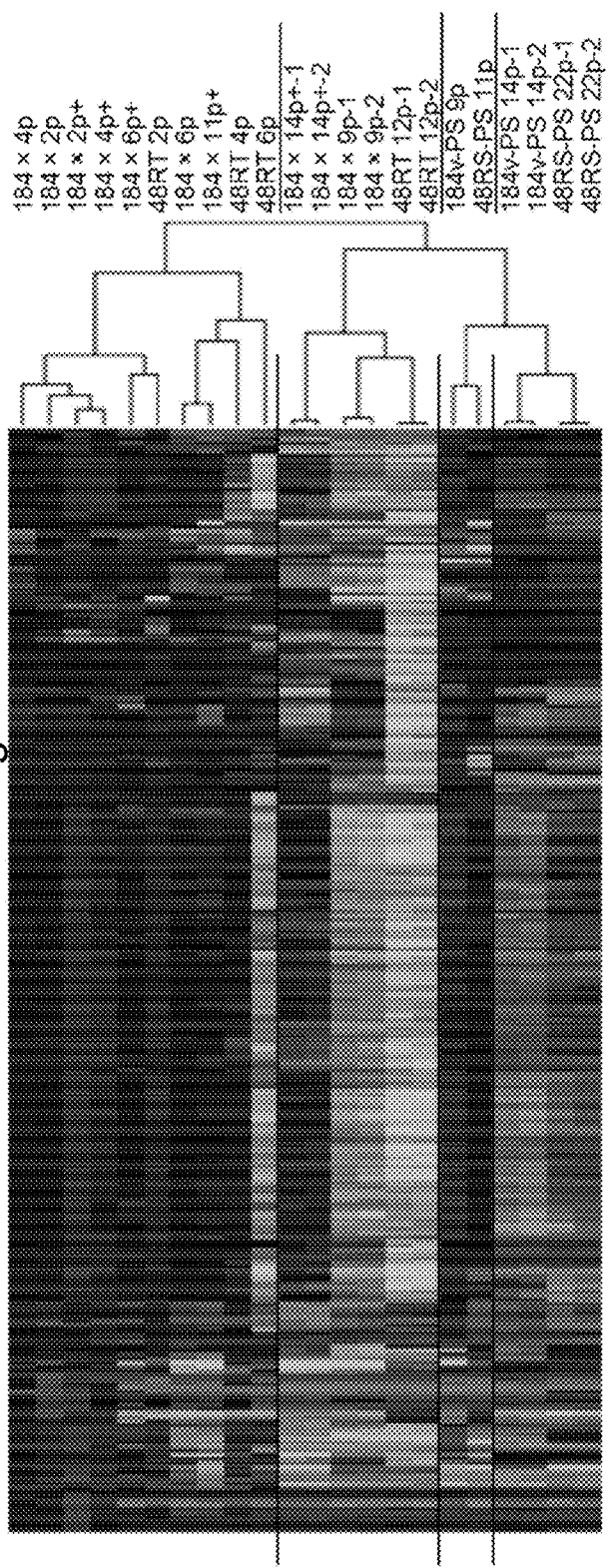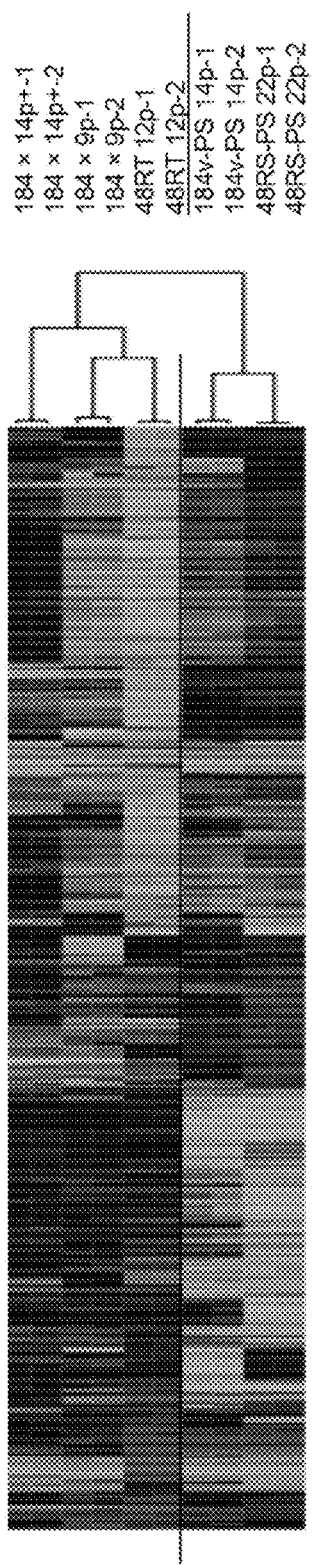
Fig.14

INCREASING CELL CULTURE POPULATION DOUBLINGS FOR LONG-TERM GROWTH OF FINITE LIFE SPAN HUMAN CELL CULTURES

CROSS-REFERENCE TO RELATED APPLICATIONS

This application is a continuation application of U.S. patent application Ser. No. 12/242,474, filed on Sep. 30, 2008, now U.S. Pat. No. 8,962,325, which claims priority from PCT Patent Application No. PCT/US2007/065718, filed on Mar. 30, 2007, which claims priority from U.S. Provisional Patent Application No. 60/788,261, filed on Mar. 31, 2006, all of which are hereby incorporated by reference in their entirety for all purposes.

STATEMENT OF GOVERNMENTAL SUPPORT

This invention was made during work supported by NIH grant CA-24844, NIH grant U54 CA112970-01 and the U.S. Department of Energy under Contract No. DE-AC02-05CH11231. The government has certain rights in this invention.

BACKGROUND OF THE INVENTION

1. Field of the Invention

The present invention relates to cell lines, cell cultures, compositions and cell culture media. More specifically, the present invention relates to methods to develop new cell lines and to increase cell culture population doublings of finite life span human cells. The present invention also relates to using the described cell cultures and methods for assessment of factors influencing aging and/or carcinogenesis.

2. Related Art

Human mammary epithelial cells (HMEC), the cell type from which breast cancers originate, normally express a finite reproductive potential in culture. This cellular senescence can be enforced by the repression of telomerase, the enzymatic activity that allows cells to maintain the integrity of the chromosome ends, as well as by a stress-induced mechanism (stasis), and by exposure to overexpressed oncogenes (OIS: oncogene-induced senescence). Telomerase expression is found in cancer cells; the resultant immortality allows cancers to accumulate the errors necessary for malignancy. Thus, telomerase repression is thought to be a tumor suppressor mechanism. Low telomerase expression may be present in some finite HMEC, and this telomerase activity may perform functions other than maintaining chromosomal ends.

For a normal, finite life span human breast cell to become malignant, multiple aberrations in pathways governing growth control and invasive potential need to accumulate. The errors seen in human breast cancers commonly involve defects in the retinoblastoma (RB) pathway, and almost always include reactivation of telomerase activity. The immortal potential conferred by telomerase is thought to be crucial for error accumulation, and is due to the ability of telomerase to maintain stable telomere lengths via de novo addition of telomeric repeat sequences. Expression of telomerase activity, by itself, is not thought to confer malignancy-associated properties (Morales, C. P. et al. Absence of cancer-associated changes in human fibroblasts immortalized with telomerase. Nature Gen., 21: 115-118, 1999; Jiang, W. R. et al. Telomerase expression in human somatic cells does not induce changes associated with a transformed phenotype. Nature Gen., 21: 111-114, 1999; Wei, S. et al. Expression of catalytically active telomerase does not prevent premature senescence caused by overexpression of oncogenic Ha-Ras in normal human fibroblasts. Cancer Res., 59: 1539-1543, 1999.), however, a variety of recent studies suggest that telomerase may perform non-telomere length maintenance functions that affect cell behavior (Stampfer, M. et al. Expression of the telomerase catalytic subunit, hTERT, induces resistance to transforming growth factor β growth inhibition in $p16^{INK4}(-)$ human mammary epithelial cells. Proc. Natl. Acad. Sci., USA., 98: 4498-4503, 2001; González-Suárez, E. et al. Increased epidermal tumors and increased wound healing in transgenic mice overexpressing the catalytic subunit of telomerase, mTERT, in basal keratonocytes. EMBO J., 20: 2619-2630, 2001; Oh, H. et al. Telomerase reverse transcriptase promotes cardiac muscle cell proliferation, hypertrophy, and survival. Proc Natl Acad Sci USA, 98: 10308-11033, 2001; Lu, C. L. et al. Telomerase protects developing neurons against DNA damage-induced cell death. Dev. Brain Res., 131: 167-171, 2001; Blasco, M. A. Telomerase beyond telomeres. Nat Rev Cancer, 2: 627-632, 2002; Smith, L. L. et al. Telomerase modulates expression of growth-controlling genes and enhances cell proliferation. Nat Cell Biol, 5: 474-479, 2003; Masutomi, K. et al. Telomerase maintains telomere structure in normal human cells. Cell, 114: 241-253, 2003.).

Experimental examination of certain hypotheses have previously been very difficult to perform in normal finite life span human mammary epithelial cells, or other normal finite life span human epithelial cells, due to the rapid onset of stasis once normal human epithelial cells are placed in culture. A consequence of the limited pre-stasis growth has been that studies requiring large numbers of cells, or large standardized cell batches, were difficult to perform. Most large-scale studies using cultured finite life span HMEC have employed cell cultures originally developed and termed post-selection HMEC, i.e., cells that had spontaneously silenced p16 expression, thus overcoming stasis (Brenner, A. J. et al. Increased p16INK4a expression with onset of senescence of human mammary epithelial cells and extended growth capacity with inactivation. Oncogene, 17: 199-205, 1998; Hammond, S. L. et al. Serum-free growth of human mammary epithelial cells: Rapid clonal growth in defined medium and extended serial passage with pituitary extract. Proc. Natl. Acad. Sci. USA, 81: 5435-5439, 1984.).

BRIEF SUMMARY OF THE INVENTION

The present invention provides methods and media for prolonging the proliferative life span of finite human cell cultures and increasing population doublings (PD). The present invention is built upon the premise that a distinct mechanism of senescence is due to stresses made upon the cells—and not telomere length as previously postulated. Thus, methods, processes and approaches that mitigate the experience of stress in these finite life span cultures could increase PD potential.

In one embodiment, the invention provides a method for increasing population doublings in a cell culture of human epithelial cells with finite life span, comprising the steps of providing a cell culture of pre-stasis human epithelial cells and providing a cell culture medium comprising a ratio of medium with serum and serum-free medium to the cell culture, wherein each of the media are optimized for a specific type of human epithelial cell, whereby population doublings and finite life span of the cell culture are increased as compared to a control.

The present invention further provides a cell culture medium for culturing pre-stasis human mammary epithelial cells comprising a ratio of a medium with serum and a serum-free medium, whereby the cell cultures exhibit a prolonged lifespan and increased population doublings. In one embodiment, the medium with serum may or may not contain conditioned media.

In another embodiment, the present method can be used to prolong the life span of other types of cell cultures from human epithelial cells from various normal tissues including prostate, ovarian, endometrial, skin, bronchial, lung, thyroid, intestinal, esophogeal epithelial cells, melanocytes or human cell cultures derived from endothelial muscle or connective (fibroblasts) tissues. In a preferred embodiment, the human epithelial cells are human mammary epithelial cells (HMEC).

In a preferred embodiment, each of the media is optimized for extended growth of a specific type of human epithelial cell. The cell culture media can be optimized and vary in concentration of compounds including but not limited to, EGF, hydrocortisone, bovine pituitary extract, estradiol, tri-iodothyronine, insulin or insulin-like growth factor, bovine serum albumin, or serum.

In some embodiments, the medium with serum is MM medium. In some embodiments, the medium with serum is MM4 medium. In another embodiment, the serum-free medium is MCDB170.

In some embodiments, the ratio of medium with serum and serum-free medium is between 30% to 60% medium with serum and 40% to 70% serum-free medium. In one embodiment, the ratio is 50% medium with serum and 50% serum-free medium. In another embodiment, the ratio is 30% medium with serum and 70% serum-free medium. In another embodiment, the ratio is 60% medium with serum and 40% serum-free medium.

In one embodiment, the method further comprises the step of providing an effective amount of an anti-stress associated compound to the cell culture, whereby the population doublings and finite life span of the cell culture are further increased. In another embodiment, the anti-stress associated compound is added to the primary passage of the cell culture. In another embodiment, the anti-stress associated compound is added at or after the second passage of the cell culture. In yet another embodiment, the means for reducing cell stress is to provide an environment for the cells that maintains pH, increases gas exchange and polarity, or to provide a three-dimensional environment for cell growth.

In a preferred embodiment, the anti-stress associated compound is oxytocin, wherein an effective amount of oxytocin is a concentration between 0.05 nM and 5.0 nM, even more preferably about 0.1 nM. Thus, the present invention also provides a method for prolonging the life span of human cell cultures and increasing population doublings, comprising the steps of providing a cell culture that is pre-stasis and providing an effective amount of oxytocin to said cell culture, whereby the population doublings and finite life span of the cell culture are increased as compared to a control. In one embodiment, a second anti-stress associated compound can be added in addition to an effective amount of oxytocin.

The anti-stress associated compound can include but is not limited to, oxytocin, bovine serum albumin (BSA), angiotensin II, serotonin (5-HT), melanin concentrating hormone, histamine, bombesin and gastrin-releasing peptide (GRP), glucagons-like peptide-1 (GLP-1), cholecystokinin (CCK), dopamine, and corticotrophin releasing factor. In another preferred embodiment, the anti-stress associated compound is bovine serum albumin (BSA).

The method can further comprise the step of adjusting $O_2$ levels of the cell culture between 3% and 20%, whereby the $O_2$ levels optimize population doublings and prolong finite life span.

In another aspect, the present invention provides the ability to grow these normal pre-stasis cells for increased PD for studies to test and quantify the pro or anti aging or cancer-promoting capacity of many kinds of factors. It is an object of the present invention to provide a culture model to study how certain factors affect overall PD potential as well as the capacity to overcome the stasis senescence barrier and/or the OIS barrier.

Another object of the present invention is to provide media for easier derivation of immortally transformed lines from pre-stasis HMEC than post-selection HMEC. Thus, the invention also provides methods for easier generation of transformed HMEC cell lines.

BRIEF DESCRIPTION OF THE DRAWINGS

FIG. 5 is a set of photographs showing a comparison of LI and p16 expression in pre-stasis HMEC from specimen 184, batch ◇, grown in M85±oxytocin and assayed at the same day post-plating in culture. Note that the culture with oxytocin, although at 2 passages beyond the culture without oxytocin, shows more proliferative cells and fewer cells with the stasis-associated senescent morphology (large, flat, vacuolated, p16+).

FIG. 12 is a (A) graph showing the effect on growth and p16 expression of switching pre-stasis 184 HMEC, batch F, from M85 to MM. (B) Graph showing extended pre-stasis growth of 184 HMEC, batch F, in M85 with oxytocin added at passage 4. (C) Photographs of the corresponding cell cultures of (A) and (B) at each of the noted passages. All photomicrographs were taken at 40× magnification.

FIG. 14 is a heat map showing unsupervised cluster analysis of gene expression patterns in growing pre-stasis and post-selection HMEC and HMEC at stasis or agonescence. (A) Unsupervised clustering of growing and senescent (stasis or agonescence) HMEC from specimens 184 and 48R showing a partial probe set. (B) Unsupervised clustering of senescent (stasis or agonescence) HMEC from specimens 184 and 48R showing a partial probe set; 529 probe sets were used for the clustering.

DETAILED DESCRIPTION OF THE PREFERRED EMBODIMENT

1. Introduction

Figure 1:
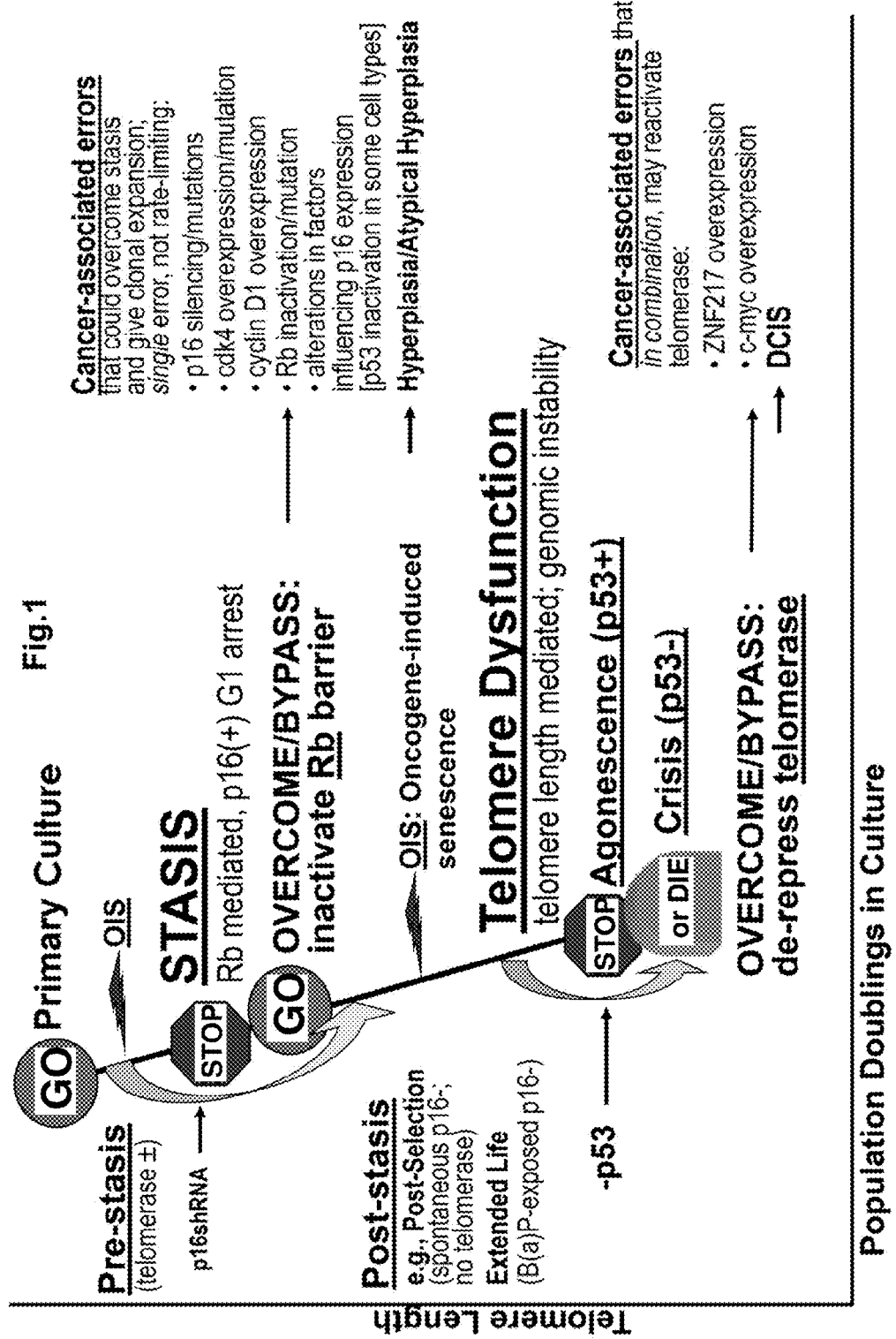
FIG. 1 is a model of HMEC Senescence Barriers (and cancer-associated errors) showing a comprehensive picture of HMEC senescence and immortalization that offers some new perspectives on underlying mechanisms, including the role of telomerase expression and stress, and is consistent with what is known about carcinogenesis pathways in vivo.

The present invention provides methods for increasing population doublings (PD) and finite life spans of pre-stasis human epithelial cells. The invention also provides cell culture media for growing the same. The invention is based upon the discovery of a new model for human mammary epithelial cell senescence and immortalization.

2. A New Model for HMEC Senescence and Immortalization

The goal of the research of the inventors has been to develop an HMEC system to understand the normal processes governing HMEC growth, differentiation, and aging, and how these normal processes are altered during immortal and malignant transformation. The inventors' approach has focused on overall system development, and generation of a large-scale picture of the many steps involved in breast carcinogenesis. The logic has been that understanding a process as complex as cancer progression will be greatly aided by a comprehensive picture that allows all the pieces of this puzzle to be viewed in dynamic relationship.

The present invention describes that studies using the extensive HMEC culture system have led to the postulation that cultured HMEC encounter two mechanistically distinct barriers to unlimited proliferation. These senescence barriers, described below, suppress immortalization and thus prevent tumor progression. Acquiring the errors that allow these barriers to be overcome appears critical for breast cancer progression.

Understanding of the factors influencing normal human breast biology is constrained by the limitations of currently available, experimentally tractable normal HMEC culture systems. One significant constraint is the small number of population doublings (PD) achieved by epithelial cells that are derived from normal tissues prior to undergoing a stress-associated senescence arrest (stasis). Pre-stasis HMEC refers to cells in culture prior to undergoing stasis. As a consequence of the limited pre-stasis PD, studies requiring a large number of cells, or large standardized cell batches, were difficult to perform. Pre-stasis HMEC are most reflective of the cell types seen in normal human breast tissues; therefore efforts were directed to improve conditions for growth of pre-stasis HMEC once the distinct nature of the stasis and telomere dysfunction senescence barriers became apparent.

The generic terms "senescence" and "replicative senescence" have been widely used but lack precisely defined molecular correlates. The lack of molecularly defined nomenclature for the senescence barriers in culture has impeded understanding, particularly of the potential role of stasis in vitro and in vivo. In turn, this situation has obscured the importance of determining what induces stasis in vitro, how to obtain culture conditions that will delay the onset of stasis, the molecular mechanisms responsible for stasis, and how stasis and overcoming it affect carcinogenesis.

Once the distinct nature of the stasis and telomere dysfunction senescence barriers became apparent, the critical importance of being able to grow pre-stasis HMEC for greater population doublings was recognized. By optimizing pre-stasis HMEC culture and characterizing resultant populations, described herein are changes in culture conditions, such as exposure to the anti-stress peptide oxytocin, that greatly increase pre-stasis cell culture proliferation. An increase in cell culture proliferation further provides substrates for research, study, and for assays to examine factors that may influence carcinogenesis and/or aging.

Long-term studies have generated a new paradigm of HMEC senescence and immortalization. Referring now to FIG. 1, this comprehensive model offers new perspectives on potential underlying mechanisms, including the role of telomerase expression and stress, and is consistent with what is known about carcinogenesis pathways in vivo (Chin, K. et al., In situ analysis of genome instability in breast cancer. Nature Genetics, 36: 984-988, 2004.; Stampfer, M. R. and Yaswen, P. Human epithelial cell immortalization as a step in carcinogenesis. Cancer Lett, 194: 199-208, 2003.). It is possible that many factors that influence breast pre-neoplasia may act on pre-stasis cells, and the potential roles of these factors have been obscured by the lack of good culture systems for pre-stasis HMEC.

Herein are described culture conditions that permit sufficient pre-stasis PD to allow generation of large standardized cell batches and examination of normal human epithelial cells prior to the onset of stasis.

3. Media and Method for Increasing Population Doublings

In one embodiment, the invention provides a method for increasing population doublings in a cell culture of human epithelial cells with finite life span, comprising the steps of providing a cell culture of pre-stasis human epithelial cells and providing a cell culture medium comprising a ratio of a medium with serum and a serum-free medium to the cell culture, wherein each of the media are optimized for a specific type of human epithelial cell, whereby population doublings and finite life span of the cell culture are increased as compared to a control.

By control, it is intended to mean a cell culture that has been provided with a medium previously used to grow pre-stasis human epithelial cells, such as a medium with serum (e.g., MM), a serum-free medium (e.g., MCDB170), or a commercially available medium (e.g., EpiLite media available from Cascade Biologics). Examples of MM and MCDB170 controls are shown schematically in FIG. 2. In the present examples using human mammary epithelial cells, it was shown that HMEC undergo a variable number of PD prior to encountering stasis, depending upon culture conditions. HMEC placed in a medium containing ~1% serum and conditioned media (i.e. MM: 70% fresh and 30% conditioned) have active growth for ~15-30 PD; cells grown in a serum-free medium (i.e. MCDB170) show active proliferation for ~10-20 PD.

In a further embodiment, the invention provides a medium for culturing pre-stasis human mammary epithelial cells comprising a ratio of a medium with serum and a serum-free medium, whereby the cell cultures exhibit a prolonged life span and increased population doublings.

The increased PD and finite life span allows large standardized batches of cells to be grown and stored frozen to permit reproducible testing of potential pro or anti aging or cancer-promoting factors using the same starting cell population. In one embodiment, the present invention provides the ability to grow these normal pre-stasis cells for increased PD for studies to test and quantify the pro or anti aging or cancer-promoting capacity of many kinds of factors. The present invention provides a culture model to study how certain factors affect overall PD potential as well as the capacity to overcome the stasis senescence barrier and/or the OIS barrier.

a. Types of Human Epithelial Cells

The presently described method can be used to prolong the life span of various types of cell cultures from human epithelial cells from various normal tissues including but not limited to, mammary, prostate, ovarian, endometrial, skin, bronchial, lung, thyroid, intestinal, esophogeal epithelial cells, melanocytes or human cell cultures derived from endothelial muscle or connective (fibroblasts) tissues.

In a preferred embodiment, the cell culture is comprised of pre-stasis human mammary epithelial cells. These cells can be made readily available for breast cancer researchers similar to the post-stasis post-selection HMEC cultures developed earlier and currently in widespread use and commercially available.

In one embodiment, the present invention provides media for easier derivation of immortally transformed lines from pre-stasis HMEC rather than post-selection HMEC. Thus, the invention also provides methods for easier generation of transformed HMEC cell lines.

b. Cell Culture Medium

The cell culture medium comprises a ratio of a medium with serum and a serum-free medium. In the preferred embodiment, the ratio is 50% medium with serum and 50% serum-free medium. In another embodiment, the cell culture medium may be optimized by varying ratios of media with serum and serum-free media between 30-60% medium with serum and 40-70% serum-free medium, respectively. For example, in some embodiments, the ratio is 30% medium with serum and 70% serum-free medium. In other embodiments, the ratio is 60% medium with serum and 40% serum-free medium.

In one embodiment, the medium with serum may contain conditioned media. In one embodiment, the medium with serum that contains conditioned medium is MM medium. The MM medium has been characterized in Stampfer, M, Hallowes, R, Hackett, A J, Growth of normal human mammary epithelial cells in culture, *In Vitro* 16:415-425, 1980 and Stampfer, M R, Cholera toxin stimulation of human mammary epithelial cells in culture, *In Vitro* 18:531-537, 1982, and is available from the inventors. The cells and media are also described by M. Stampfer, H. Smith, A. Hackett, in U.S. Pat. No. 4,423,145, Enhanced Growth Medium and Method for Culturing Human Mammary Epithelial Cells, issued Dec. 27, 1983, hereby incorporated by reference.

As described in U.S. Pat. No. 4,423,145, MM media has a preferred composition as follows:

| ENHANCED GROWTH MEDIA Concentration in Basal Media[1] | | |
|---|---|---|
| Component | Effective Range | Preferred Range |
| Insulin | 0.1-20 µg/ml | 5-10 µg/ml |
| Hydrocortisone | 0-10 µg/ml | 0.05-0.15 µg/ml |
| Epidermal Growth Factor | 0-20 ng/ml | 3-8 ng/ml |
| 74Int CM[2] | 10-50% | 25-35% |
| 767B1 CM[2] | 10-50% | 25-35% |
| 578Bst CM | 0-20% | 5-15% |
| Estradiol | $0\text{-}10^{-7}$M | approximately $10^{-9}$M |
| Triiodothyronine | $0\text{-}10^{-7}$M | approximately $10^{-8}$M |
| Cholera Toxin | 0.1-1000/ng/ml | 1-10 ng/ml |
| Serum | 0-3% | 0.2-0.7% |

[1] The basal medium is a conventional minimal essential medium such as Ham's F-12 or Dulbecco's Minimal Essential Medium.
[2] The concentrations of both 74Int and 767B1 are additive. The desired concentration may be provided by either 74Int CM or 767B1 CM alone, or in combination.

MM medium is comprised of 30% conditioned media and 70% fresh medium. The conditioned media has already been used to grow other human epithelial cells and is added to fresh media because cells secrete growth and other factors into conditioned medium that promoted better cell growth (Stampfer et al., *In Vitro* 16:415-425, 1980). The conditioned media is comprised of about 50% DMEM media and 50% Ham's F12 media (Invitrogen). Added to this mixture is 5% fetal bovine serum, and insulin. Two cell lines (767BL and 578BST) are fed with this medium for about 2 days, the conditioned medium is collected and filtered to make the MM medium. The fresh medium is comprised of 50% DMEM medium and 50% Ham's F12 medium (Invitrogen), and then added to the conditioned media for a final mixture of about 30% conditioned media and 70% fresh medium. Epidermal growth factor (EGF), hydrocortisone, estrogen, triiodothyronine, fresh fetal bovine serum 0.5%, and more insulin are added.

In a preferred embodiment, each of the media is optimized for extended growth of a specific type of human epithelial cell to be cultured. The cell culture media can be optimized and vary in concentration of compounds including but not limited to, EGF, hydrocortisone, bovine pituitary extract, estradiol, triiodothyronine, insulin or insulin-like growth factor, bovine serum albumin, or serum.

In some embodiments, the medium with serum is not conditioned. For example, MM4 medium is MM medium lacking the conditioned media. MM4 medium is 100% fresh medium.

In a preferred embodiment, the serum-free medium is MCDB170. The MCDB170 medium is commercially available and has been characterized in Hammond, S L, Ham, R G, and Stampfer, M R, Serum-free growth of human mammary epithelial cells: rapid clonal growth in defined medium and extended serial passage with pituitary extract, *Proc Natl Acad Sci* (USA) 81:5435-5439, 1984. Methods describing the use of these media in the isolation and growth of human cell cultures are also described in Stampfer, M R, Isolation and growth of human mammary epithelial cells. *J Tissue Cult. Meth.* 9:107-116, 1985, hereby incorporated by reference.

In another embodiment, the serum-free media is the commercially available MEGM media (Clonetics Division of Lonza). This medium, however, may need to be supplemented with factors found in MCDB170. If bicarbonate free MEGM is used in lieu of MCDB170, with HEPES free DMEM/F12, 5% $CO_2$ should be used. In another embodiment, if bicarbonate free MEGM is used with +bicarbonate +HEPES DMEM/F12, then the $CO_2$ concentration should be lowered to about 1%.

i. M85 Media

Figure 2:
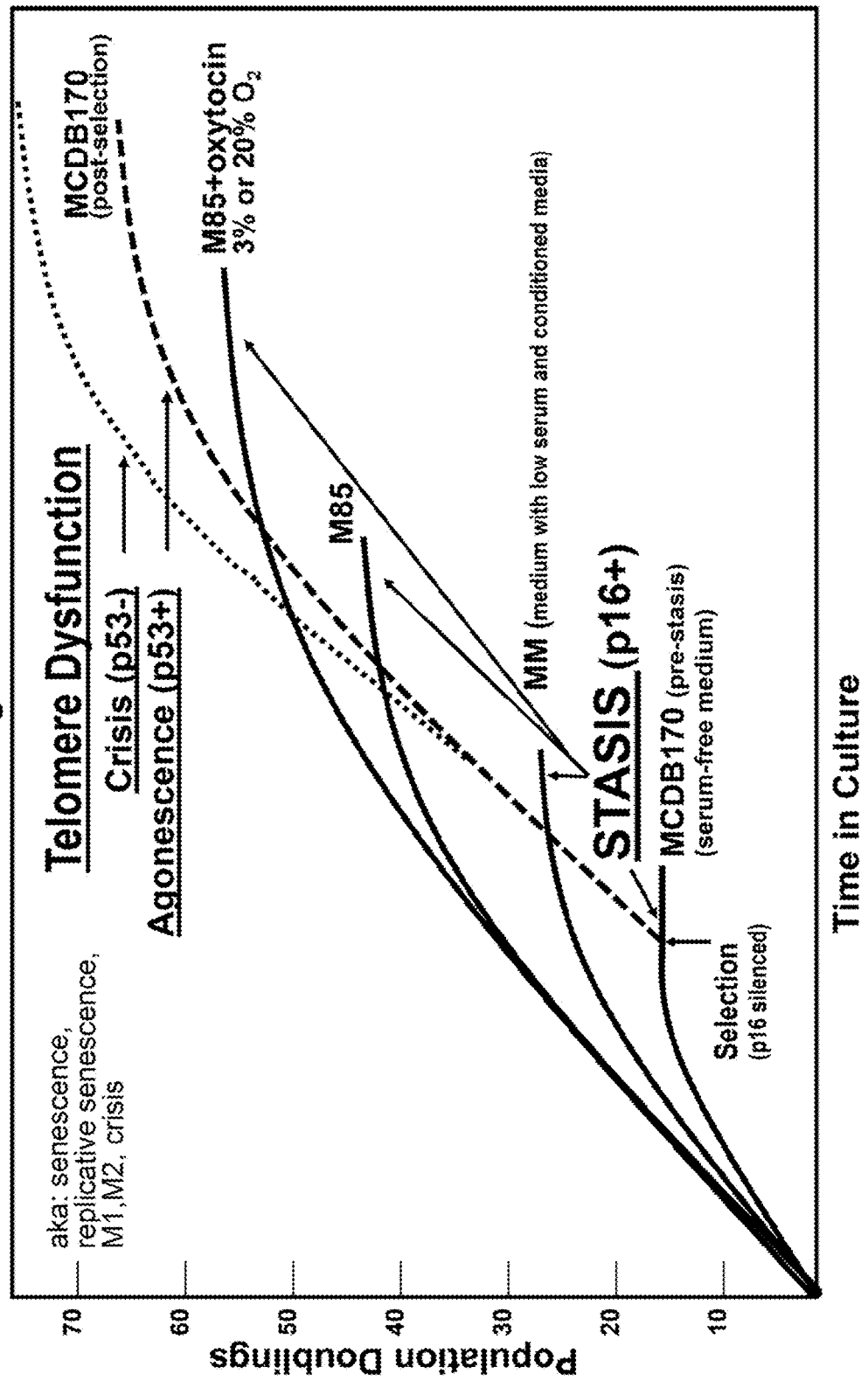
FIG. 2 is a schematic representation of growth of pre-stasis and post-selection HMEC under differing culture conditions. Total PD achieved by pre-stasis HMEC varies greatly depending upon culture conditions employed.

In one embodiment, the cell culture medium is M85 media. The Examples described herein show that M85, comprised of both MM and MCDB170, enabled pre-stasis HMEC to grow for up to ~45 PD. As shown in FIG. 2, this is a drastic increase compared to MM or MCDB170 used alone. The M85 medium was seen to provide increased PD for pre-stasis HMEC from 3 individuals, 184, 48, and 240 as compared to MM, MCDB170, or the commercial EpiLife alone. In another embodiment, the M85 medium may vary in the concentration of other components such as hydrocortisone or BPE. In other embodiments, cAMP stimulators may be added to the primary culture or in the first few passages of culture. For example, in a preferred embodiment, cholera toxin may be added to the MM not in primary culture, but during passage 2. In another embodiment, the MCDB170 medium may or may not include isoproterenol for use as a cAMP stimulator. Generally, MCDB170 used for HMEC culture has serum free supplements which may be cell type specific. The M85 media should be properly buffered for 5% $CO_2$.

ii. M87 Media

In another embodiment, the cell culture medium is M87. M87 medium is comprised of MM4 medium and MCDB170 medium. In a preferred embodiment, M87 medium is comprised of about equal parts MM4 and MCDB170 media (50:50). In another embodiment, upon further optimization, the M87 medium may be comprised of varying ratios of MM4 and MCDB170 media. For example, in some embodiments, the M87 medium may be comprised of 60% MM4 and 40% MCDB170, or 30% MM4 and 70% MCDB170. In another embodiment, the M87 medium may vary in the concentration of other components such as hydrocortisone or BPE. The M87 medium should also be properly buffered for 5% $CO_2$.

Figure 8:
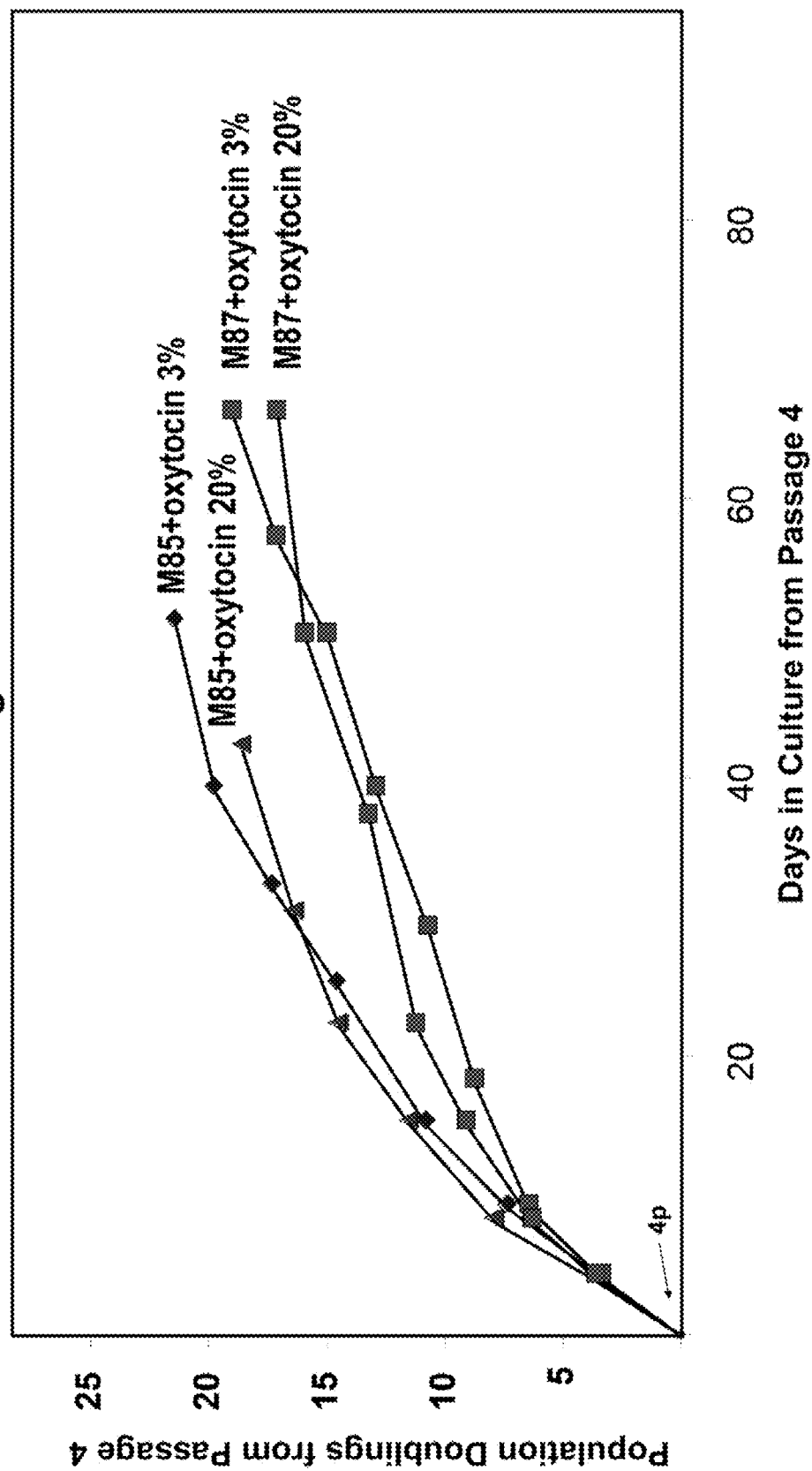
FIG. 8 is a graph showing the effect of different oxygen concentration and presence of conditioned media (CM) on growth of pre-stasis HMEC from specimen 184, batch F.
Figure 9:
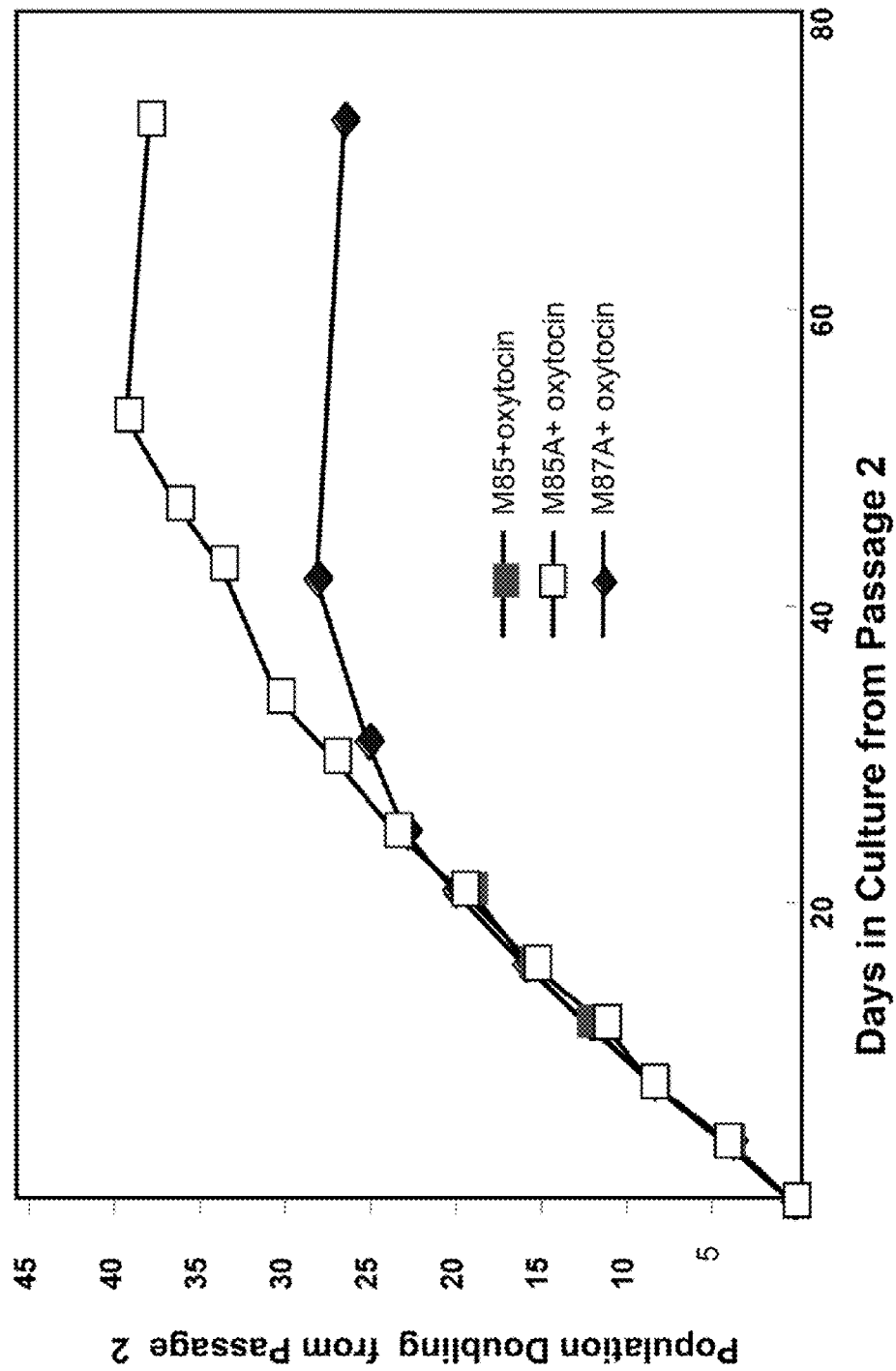
FIG. 9 is a graph showing the effect of switching pre-stasis 184◇ HMEC, grown in M85 in primary culture, to different media at passage 2.
Figure 10:
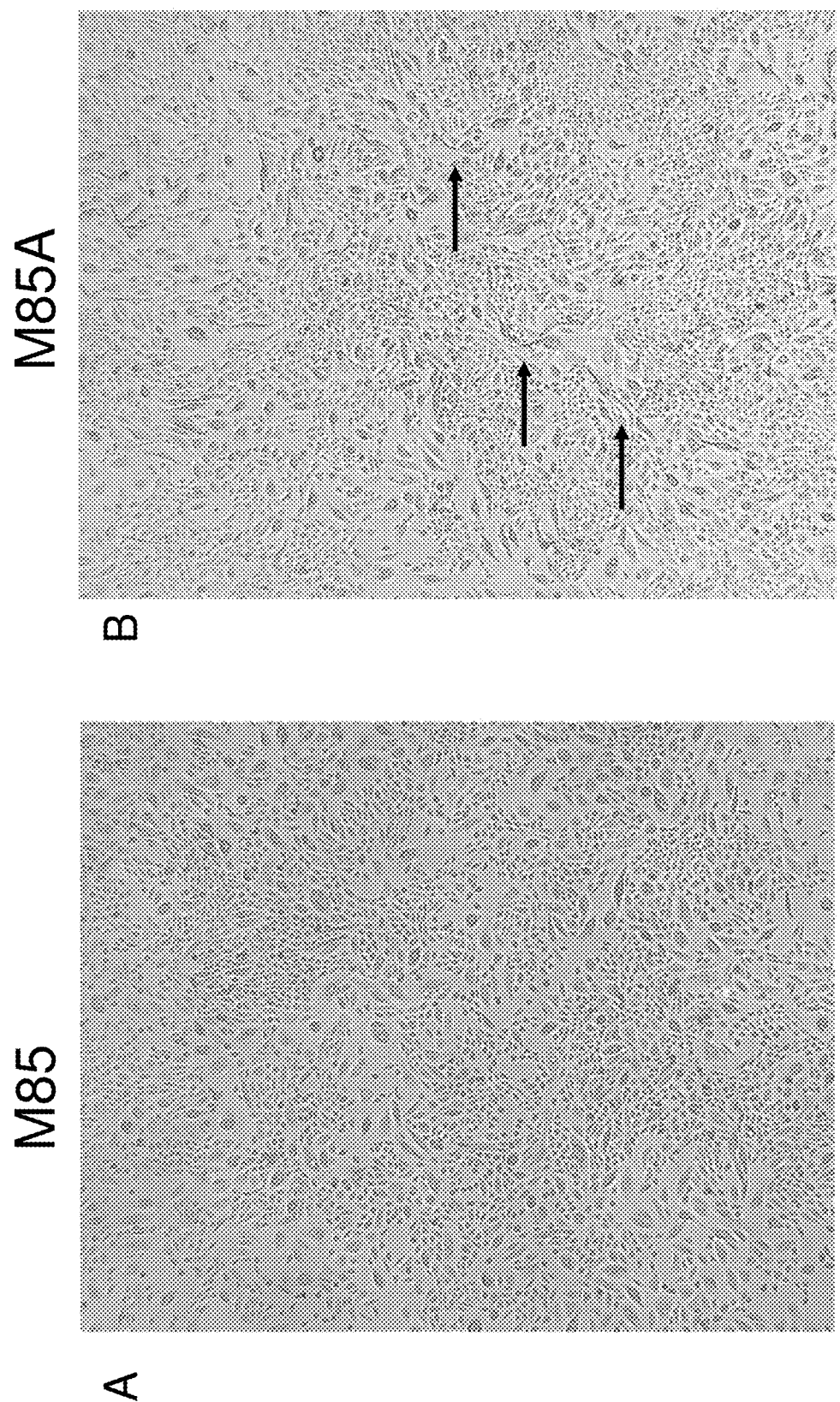
FIG. 10 shows photographs of the morphology of 184◇ HMEC grown in M85+oxytocin vs. M85A+oxytocin since passage 2. (A) Cells grown in M85+oxytocin. (B) Cells grown in M85A+oxytocin (in the presence of BSA) consistently showed a different morphology, with more cells with a morphology that was elongated "curly" with overgrowth of cells (arrows). These data indicate that small changes in media composition may preferentially support proliferation of different pre-stasis cell types.
Figure 13:
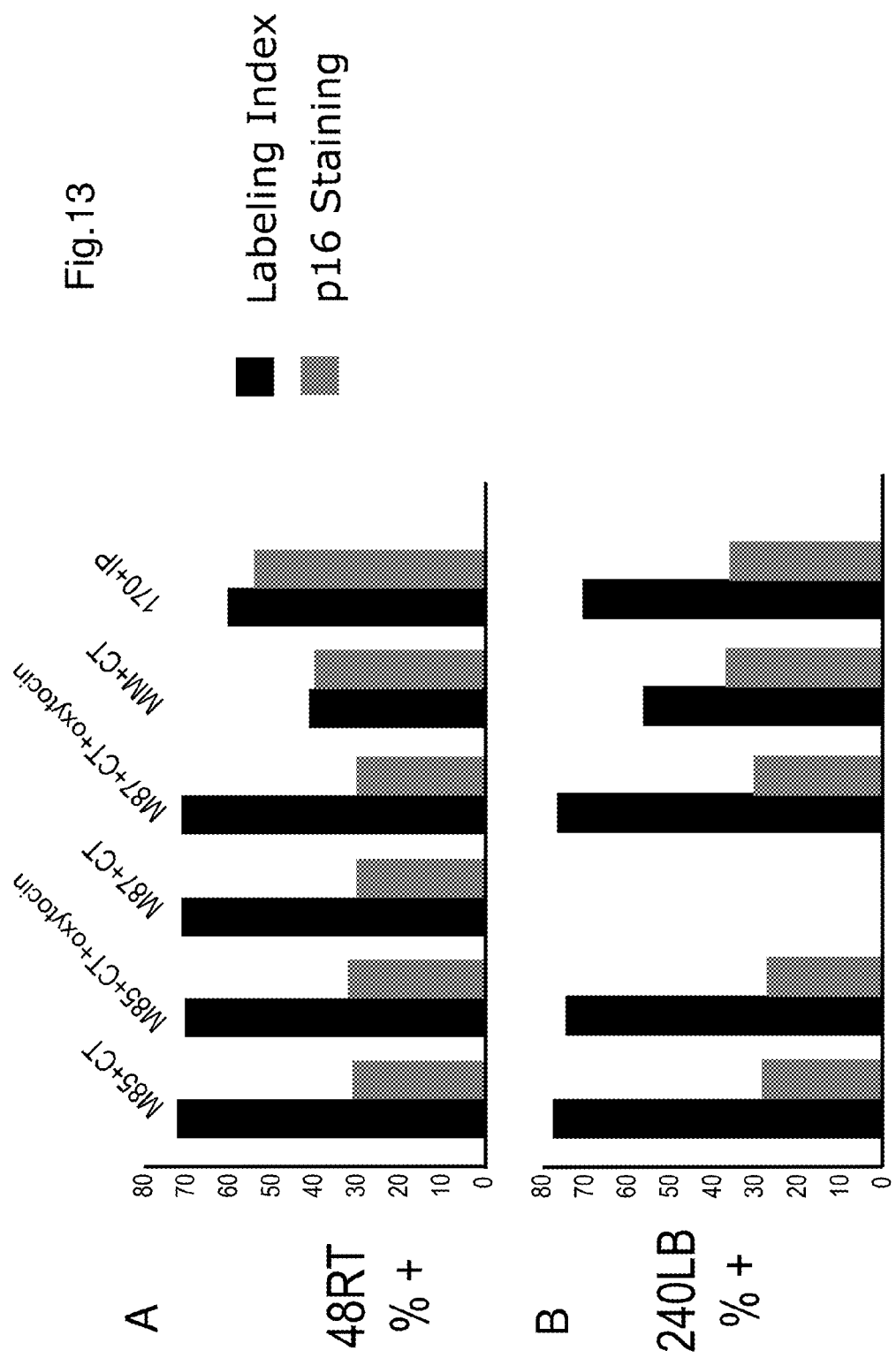
FIG. 13 is a set of graphs showing the effect of switching pre-stasis HMEC grown in M85+oxytocin at passage 5 to different media. (A) 48RT and (B) 240LB were switched to the indicated media at passage 5, subcultured to passage 6, and then assayed when midconfluent for LI and p16 expression.

Referring now to FIGS. 8, 9, and 13, M87 also enables increased growth of pre-stasis HMEC when used with an anti-stress compound which is described supra. The lack of need for conditioned medium makes M87 medium more readily available for others to use and increases commercialization. While M87 did not support as rapid growth, and may not allow as many total PD as M85, growth was comparable to M85 until passage 8.

c. Cell Culture Optimization

A variety of approaches to further increase PD can be employed, as long as one understands the basis is reduction of a cellular stress response. Known growth promoting cell culture additions and components may be added to increase population doublings and should also be tested for effectiveness or optimal concentration. The concentrations of specific media components (e.g., EGF, hydrocortisone, bovine pituitary extract, estradiol, triiodothyronine, insulin or insulin-like growth factor, serum, oxytocin, bovine serum albumin, as well as the conditioned media) can be systematically altered and selected media components (e.g., the different conditioned medium that are part of the MM formulation) are removed and assayed for resulting growth.

In one embodiment, the method further comprises the step of providing an effective amount of an anti-stress associated compound to the cell culture, whereby the PD and finite life span of the cell culture are further increased. In another embodiment, different $O_2$ concentrations are systematically applied to optimize the PD. In another embodiment, the cells are grown on extracellular matrix material. In another embodiment, the means for reducing cell stress is to provide an environment for the cells that maintains pH, increases gas exchange and polarity, or provide a three-dimensional environment for cell growth.

Thus, the present invention also provides a method for prolonging the life span of human cell cultures and increasing population doublings, comprising the steps of providing a cell culture that is pre-stasis and providing an effective amount of an anti-stress compound, such as oxytocin, to the cell culture, whereby the population doublings and finite life span of the cell culture are increased as compared to a control.

i. Anti-stress Associated Compound

By effective amount, it is intended to mean a concentration of anti-stress associated compound potent enough to cause a change in the PD of the cell culture as compared a cell culture not provided with the anti-stress associated compound.

It is contemplated that compounds associated with anti-stress activity may be beneficial to increase or sustain prolonged pre-stasis cell growth. Known anti-stress compositions and compounds such as, oxytocin, lipid rich bovine serum albumin (BSA), angiotensin II, serotonin (5-HT), melanin concentrating hormone, histamine, bombesin and gastrin-releasing peptide (GRP), glucagon-like peptide-1 (GLP-1), cholecystokinin (CCK), dopamine, and corticotropin releasing factor (CRF), may be used to increase population doublings and should be tested for effectiveness or optimal concentration.

In some embodiments, the anti-stress associated compound is added to the primary passage of the cell culture. In other embodiments, the anti-stress associated compound is added at or after the second passage of the cell culture.

In a preferred embodiment, oxytocin is added to the cell culture medium to increase PD and finite life span. The nine amino acid peptide hormone, oxytocin, is known to be involved in stimulating lactation in mammalian mothers and when infused can stimulate the uterine wall to contract to begin labor. Oxytocin also plays a role in nurturing behaviors and attachment of the mother to her offspring, and has anti-stress-like effects such as reduction of blood pressure and cortisol levels. See Light K C et al, *Horm Behav*. 2005 May; 47(5):540-8, and *Biol Psychol*. 2005 April; 69(1):5-21. Epub 2004 Dec. 29.

Figure 7:
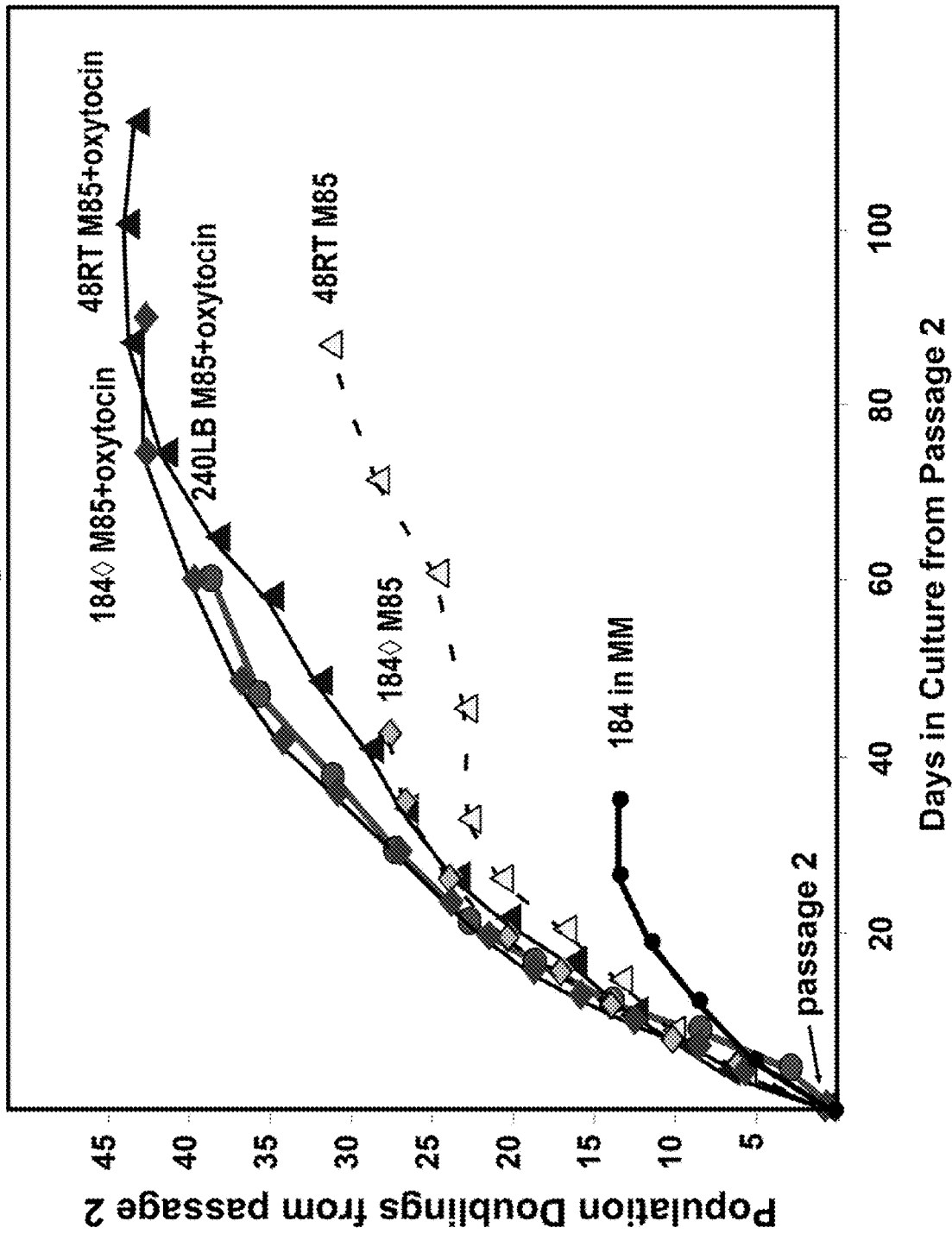
FIG. 7 is a graph showing growth of pre-stasis HMEC from 3 different individuals in M85±oxytocin.

Oxytocin was shown to extend population doublings in pre-stasis HMEC cell culture growth in an M85 base medium from about 45 PD up to about 60 PD, an increase of 33%. The addition of oxytocin was based on theoretical considerations of its anti-stress activity, and has been tested at 2 concentrations: the lower amount, 0.1 nM, provided better growth conditions than 1.0 nM, the level assayed in most breast cancer cell lines The lower concentration of 0.1 nM was also tested in 3 individual cell lines and shown to improve growth. See FIG. 7, where the increased PD shown by HMEC from specimen 184, batch ◊, is also seen in HMEC obtained from the 2 other donors tested, 48R, batch T, and 240L, batch B. Specimen 240L was grown only in M85 with oxytocin from primary organoids. Specimen 48R was grown in M85±oxytocin from primary organoids. For comparison, growth of specimen 184 in MM is shown. 184 HMEC batch ◊ and 48RT+oxytocin were grown in 20% $O_2$. The other cultures were grown in 3% $O_2$.

In a preferred embodiment, oxytocin is applied to cell cultures at final concentrations of about 0.05 nM to about 5.0 nM.

In one embodiment, oxytocin is added to the M85 medium. The potential of the M85+oxytocin medium to support long-term growth of pre-stasis HMEC will open up many new and important avenues of investigation of normal and aberrant HMEC biology. We envision even greater use of the more normal pre-stasis HMEC once it is routinely possible to culture the cells for >30 PD and thus allow for generation of large standardized cell batches, as is the current situation for the post-selection HMEC. It is expected that oxytocin may prolong pre-stasis growth of human epithelial cell types that are currently difficult to culture before stasis, and thus this addition to cell cultures during pre-stasis growth could be of widespread value. As an example, these cells can be used for standardized assay, to determine the influence of various factors on aging and/or carcinogenesis. They can also be used to understand basic mechanisms in aging, development, and/or cancer.

In another embodiment, oxytocin is added to the M87 medium. The M87 medium allows for easier access and availability of the media as compared to the M85 medium because M87 does not contain conditioned medium. This simplifies making the medium while still increasing the number of PD.

In some embodiments, bovine serum albumin (BSA) is added to the cell culture medium to increase PD and finite life span. BSA is used because of its stability, its lack of effect in many biochemical reactions, and its low cost since it is readily available in large quantities as it is purified from bovine blood, a byproduct of the beef industry. In a preferred embodiment, BSA is added to M87 medium to increase PD.

Referring now to FIG. 9, pre-stasis 184 ◊ HMEC was grown in M85 in primary culture and transferred to different media at passage 2. All cultures were switched into media containing oxytocin; one condition was M85; one condition was M85 with lipid rich BSA; one condition was M87 (no conditioned media) with lipid rich BSA. Note that the cells in M87A+oxytocin grew as well as cells in M85 until passage 8, indicating that the conditioned media can be eliminated, while maintaining good growth for many PD, although not as many PD as in the presence of the conditioned media. The cultures used in this experiment had undergone more PD in primary culture than those used for FIGS. 3-5.

It is contemplated that one or more of the other anti-stress compositions and compounds may be used instead of oxytocin, or may be used in conjunction with oxytocin. If used concurrently with oxytocin, the addition of the other anti-stress composition may be prior to or subsequent to the addition of oxytocin, in the same formulation or added simultaneously. For example, in one embodiment, BSA is added to M85, referred to as M85A. In another embodiment, oxytocin can be added to M85A. In some embodiments, BSA is added to M87, which is referred to as M87A. In another embodiment, oxytocin can be added to M87A.

ii. $O_2$ Concentration

In another embodiment, different $O_2$ concentrations are systematically applied to optimize the PD. In one embodiment, growth of these cultures in atmospheric level or low oxygen levels between 3% and 20% $O_2$ levels is used to effect small differences in overall population doubling potential. Although no significant improvement was shown in the M85 and M87 at 3% vs. 20% $O_2$ (See FIG. 8), it is contemplated that overall population doubling may be affected by different formulations of the present media and/or if different types of cells are used.

In one embodiment, the growth of these cultures are carried out in a lower oxygen environment. One example of methods for growing HMEC in MM in low $O_2$ environment is described in Yaswen, P and Stampfer, M R, Molecular changes accompanying senescence and immortalization of cultured human mammary epithelial cells, *Int. J. Biochem. Cell Biol*. 34:1382-1394 2002, which is hereby incorporated by reference. Another recent methods reference describing the culture of mammary cells is Stampfer, M R, Taylor-Papadimitriou, J, and Yaswen, P., Culture of human mammary epithelial cells, in Culture of Epithelial Cells, $2^{nd}$ Edition, Ed. Freshney, I., Wiley-Liss, 2002, which is also hereby incorporated by reference. Referring to FIG. 8, these cultures were started as organoids in MM and switched to M85+oxytocin in 3% $O_2$ at passage 2. At passage 4 they were switched to growth in 20% vs. 3% $O_2$, in either M85 or M87 medium. Growth in the absence of conditioned medium was similar for 2 passages and then cells grown without conditioned medium showed decreased proliferation.

iii. Matrix Material

In another embodiment, the cells are grown on extracellular matrix material, such as MATRIGEL, laminin or other extracellular components, including peptides that effect signal transduction of cellular receptors for extracelullar matrix ligands. In another embodiment, the cells are grown on culture dishes that allow better air flow, such as LUMOX dishes (Greiner Bio-One GmbH, Monroe, N.C.).

Figure 18:
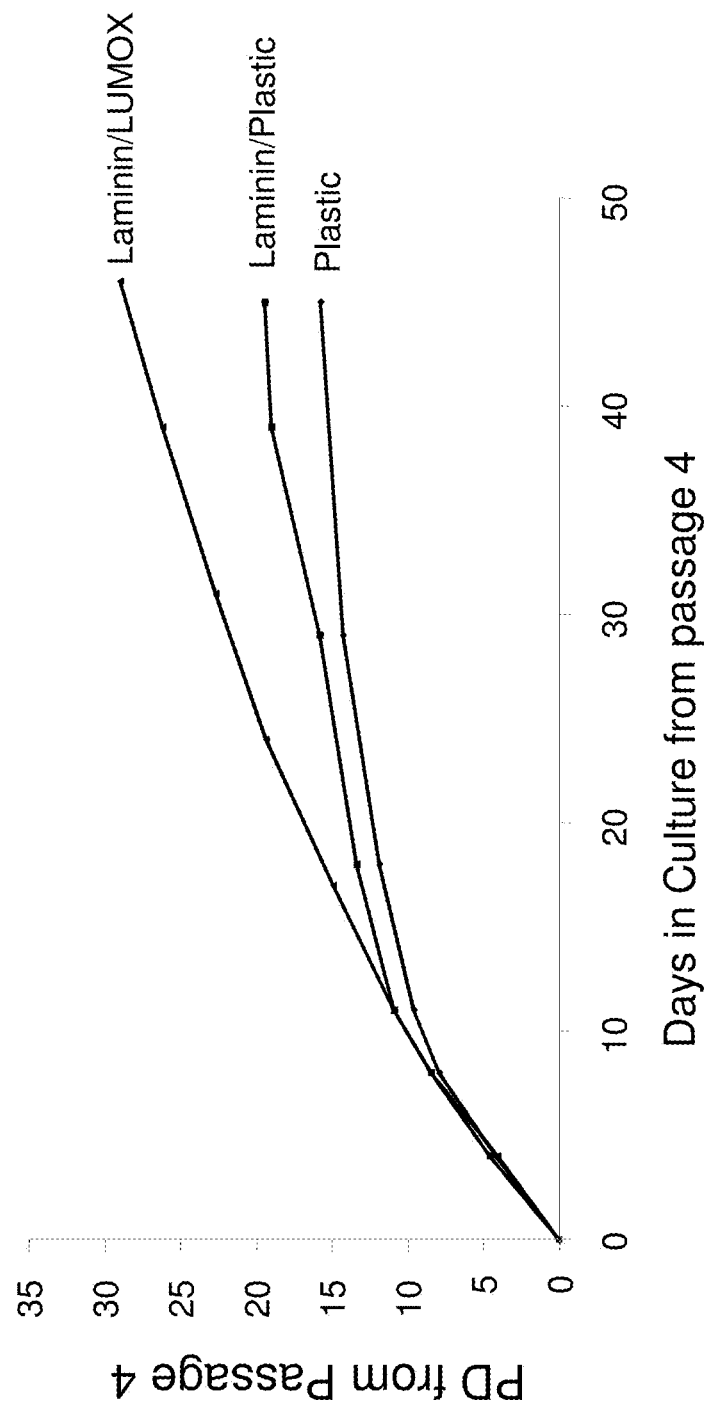
FIG. 18 is a graph showing growth of 184 HMEC, batch F, on different substrates: plastic (♦), laminin on plastic (■), or laminin on LUMOX dishes (▲). Cells were grown in MM in primary culture and switched to M85 at passage 2. At passage 4 they were switched to M87 and grown on plastic, laminin on plastic, or laminin on LUMOX dishes (which allow the cells to grow on a gas-permeable substrate).

Referring to FIG. 18, 184 HMEC, batch f, were grown in MM in primary culture and switched to M85 at passage 2. At passage 4 they were switched to M87 and grown on plastic (♦), laminin on plastic (■), or laminin on LUMOX dishes (▲) (which allow the cells to grow on a gas-permeable substrate). Note that as the cells approach stasis, more proliferation occurred in cells grown on laminin on LUMOX.

Figure 19:
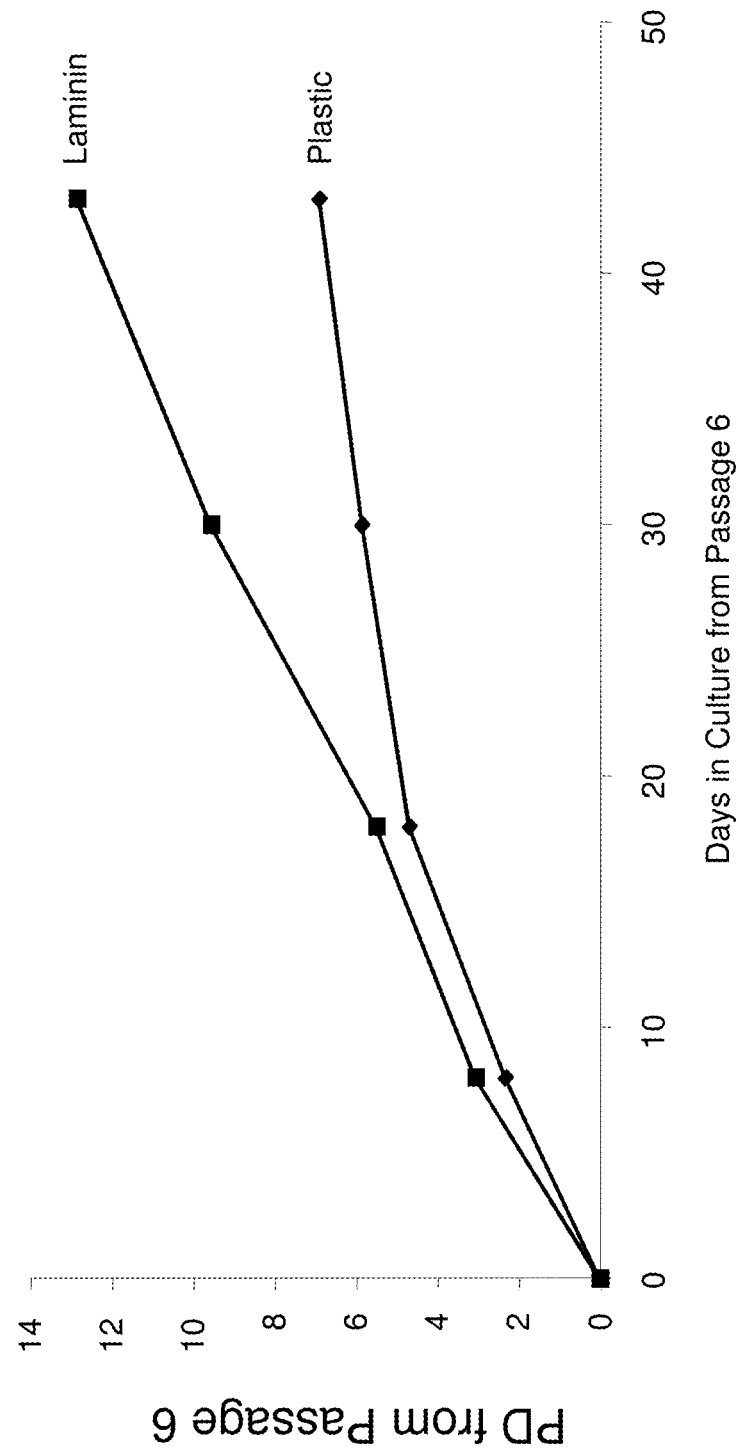
FIG. 19 is a graph showing growth of pre-stasis 48RT HMEC on different substrates: plastic (♦) or laminin on plastic (■). Cells were grown from primary culture in M85+oxytocin and switched at passage 6 to growth on laminin on plastic or plastic alone.

Referring to FIG. 19, pre-stasis 48RT HMEC were grown from primary culture in M85+oxytocin and switched at passage 6 to growth on laminin on plastic or plastic alone. Note that as the cells approach stasis, more proliferation occurred in cells on laminin.

Thus, in one embodiment, cells grown in M85±oxytocin or M85A±oxytocin medium, and M87±oxytocin or M87A±oxytocin medium are also grown on laminin or LUMOX dishes, to prolong pre-stasis growth.

4. EXAMPLES

Example 1

Increased Population Doublings in M85 Medium+Oxytocin

As shown in FIGS. 2, 3, 7-9, and 12, HMEC undergo a variable number of PD prior to encountering stasis, depending upon culture conditions. HMEC placed in a medium containing ~1% serum and conditioned media (MM) have active growth for ~15-30 PD; cells grown in a serum-free medium (MCDB170) show active proliferation for ~10-20 PD; HMEC grown in MM in a low oxygen environment (3% vs. 20%) grow for an additional ~4 PD. Recent studies have shown that a medium combining elements of MM and MCDB170 (M85) enabled pre-stasis HMEC to grow for up to ~45 PD, and addition of oxytocin to M85 at primary culture or passage 2 enabled around 60 PD total. p16 expression increases significantly ~4-6 PD prior to proliferative arrest and is expressed in almost all cells at stasis. Age dependent increased p16 expression is also observed in human breast and other tissues in vivo, suggesting that the conditions which induce it may have physiologic relevance (Nielsen, G. P. et al., Immunohistochemical survey of p16$^{INK4A}$ expression in normal human adult and infant tissues. Lab. Invest., 79: 1137-1143, 1999; Ressler, S. et al., p16INK4A is a robust in vivo biomarker of cellular aging in human skin. Aging Cell, 5: 379-389, 2006.; Kim, W. Y. and Sharpless, N. E. The regulation of INK4/ARF in cancer and aging. Cell, 127: 265-275, 2006.).

Referring now to FIGS. 12 and 13, transfer of HMEC growing in M85 that were a few passages from stasis to the more stressful MM medium resulted in rapid induction of p16 protein and growth arrest. Transfer of HMEC growing in M85+oxytocin that were >5 passages away from stasis produced only a moderate growth reduction over 2 passages. The potential of the using M85+oxytocin to support long-term growth of pre-stasis HMEC opens up many new and important avenues of investigation of normal and aberrant HMEC biology. Specifically, it will now be possible to generate large standardized batches of pre-stasis HMEC that can be used for research and/or commercial applications, for example, to test the effects of factors that could influence aging or carcinogenesis.

Figure 3:
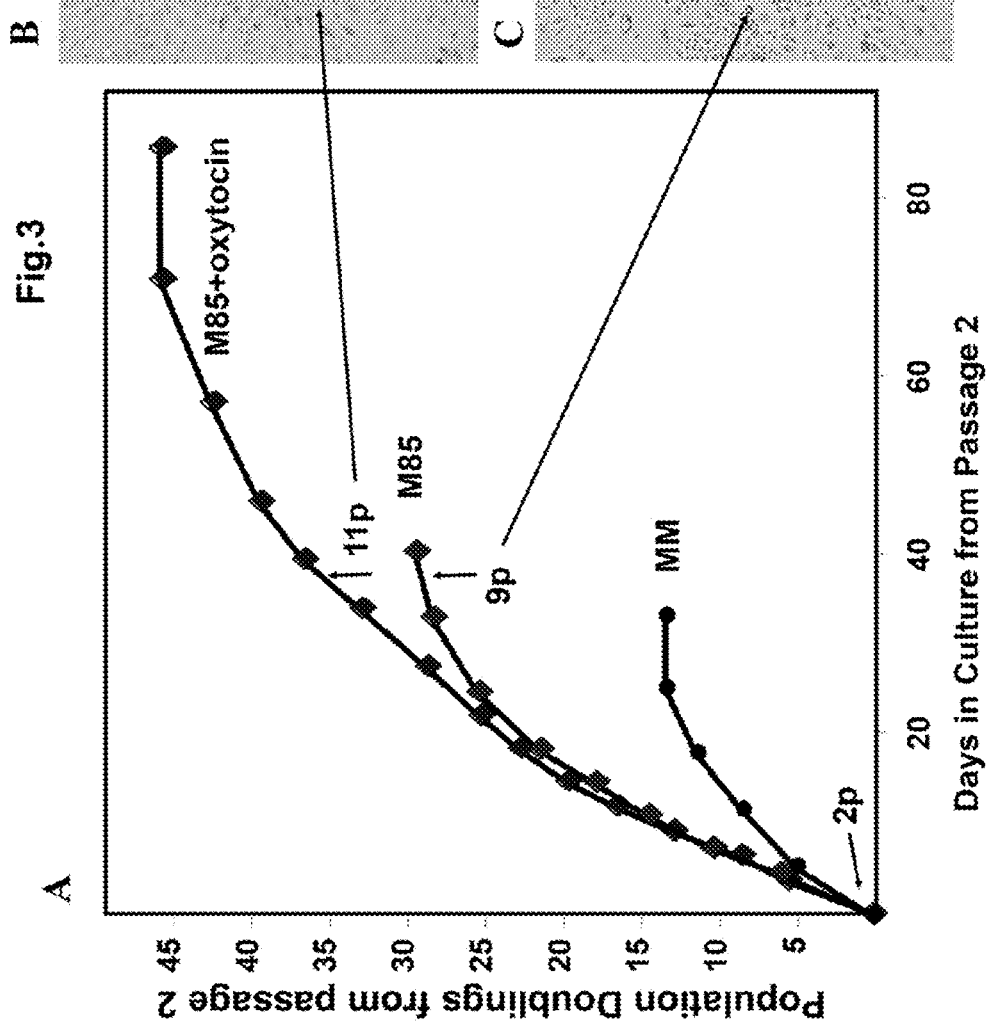
FIG. 3 is a (A) Graph showing growth of pre-stasis HMEC from specimen 184, batch ◇, from passage 2 in M85 medium with and without the presence of 0.1 nM oxytocin. Growth in MM is shown for comparison. Primary cultures were started from organoids and grown in M85 without oxytocin. The number of PD in primary culture prior to passage 2 can not be accurately determined; it can be estimated at 5-15 PD. Cell populations grown without oxytocin grew only slightly slower to start but reached stasis sooner. (B & C) Pictures of live cultures, taken on the same day (48 d post-seeding), indicate the heterogeneity of the higher passage cultures—showing a mixture of small good growing cells with larger cells more advanced towards stasis. Cells grown without oxytocin show fewer proliferative cells and more cells at advanced stasis (large, flat, vacuolated senescent morphology).
Figure 4:
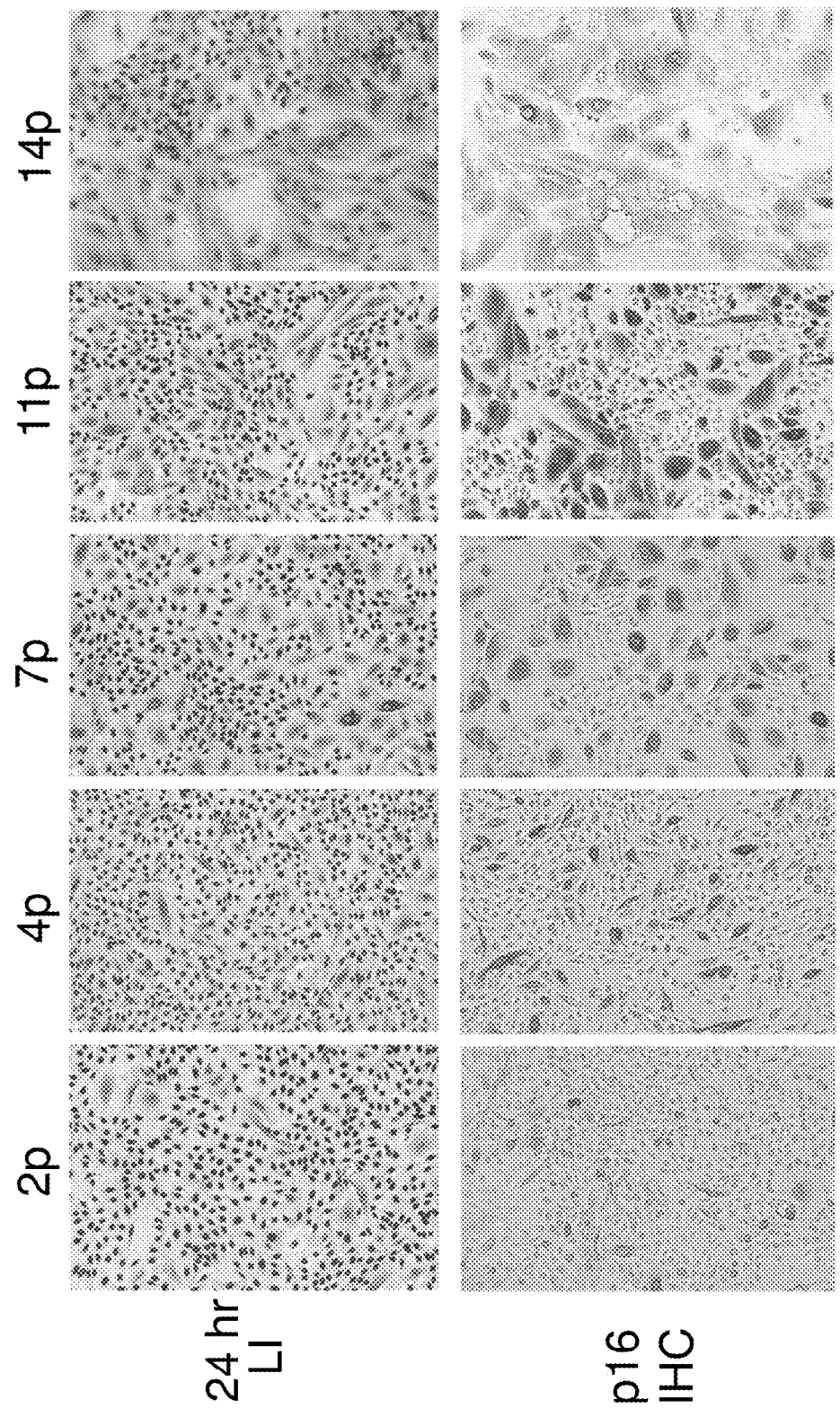
FIG. 4 shows photographs of pre-stasis HMEC from specimen 184, batch ◇, grown in M85+oxytocin and assayed at different passage levels for proliferation (DNA synthesis determined by a 24 hr exposure to BrdU and shown as labeling index [LI]) and growth arrest at stasis (measured by expression of the p16 protein as determined by immunohistochemical staining). Note the gradually increasing expression of p16 with passage and the gradual reduction in the growing population. Note also the reciprocity between positive labeling of the small cell population with BrdU and the positive staining of the larger cell population for p16 expression.

Referring now to FIGS. 3-5, which show pre-stasis growth of 184 HMEC in different media and immunohistochemical staining for p16 protein. 184 HMEC were started in M85 and subcultured at passage 2 into M85 with cholera toxin with or without oxytocin, in 20% $O_2$. Note the greatly increased PD potential in the presence of oxytocin. Note also the lower level of p16 expression and different cell morphology in HMEC cultured in M85 with oxytocin compared to a population grown without oxytocin, both at 48 days post-seeding. Note the large cells staining for p16 with the small cells still negative for p16 but positive for LI (indicative of DNA synthesis).

Referring now to FIG. 12, which shows pre-stasis growth of 184 HMEC in different media and immunohistochemical staining for p16 protein. 184 HMEC starting at 3p (experiment 1) or 2p (experiment 2) were grown in M85 in 3% $O_2$. In experiment 2, some cells were switched back to MM in 3% $O_2$ at subculture from passage 5 to passage 6. Note the lower level of p16 expression and different cell morphology in HMEC cultured in M85 at 8p vs. at stasis arrest at 11p, and the rapid increase in p16 expression when cells were transferred to MM. Post-selection 184 HMEC are shown as a negative control for p16. Note the large cells staining for p16 at 12p, as shown in FIGS. 12(B and C), with some small cells still negative. Note also the uniform expression of SA-β-gal in cells at 14p.

Referring now to FIG. 13, which shows growth and immunohistochemical staining for p16 protein of pre-stasis 48RT and 240LB HMEC were switched to the indicated media at passage 5, subcultured to passage 6, and then assayed when midconfluent for LI and p16 expression. Note that the reduction in growth (LI) and increase in level of p16 expression is much less than seen in FIG. 12, when the switched cells were closer to stasis. The absence of conditioned media, as seen in previous figures for growth curves, did not have a significant effect on LI or p16 expression over this time frame (2 passages).

In our HMEC system, it was originally observed that stasis could be spontaneously overcome in some cells grown in MCDB170, a process termed selection (Hammond, S. L., Ham, R. G., and Stampfer, M. R. Serum-free growth of human mammary epithelial cells: Rapid clonal growth in defined medium and extended serial passage with pituitary extract. Proc. Natl. Acad. Sci. USA, 81: 5435-5439, 1984). Emergent post-selection HMEC no longer express p16, associated with methylation of the p16 promoter region (Brenner, A. J., Stampfer, M. R., and Aldaz, C. M. Increased p16INK4a expression with onset of senescence of human mammary epithelial cells and extended growth capacity with inactivation. Oncogene, 17: 199-205, 1998). No spontaneous selection process in MM, M85, or M87 has yet been observed.

Example 2

Examining Pre-stasis and Post-stasis with M85+Oxytocin for the Effects of Potential Oncogenic Agents on Transformation Prior work in many laboratories has indicated that normal human epithelial cells are very refractory to in vitro transformation to immortality and/or malignancy. Most transformation studies using HMEC have employed cultures that were already post-stasis. The resultant cell lines, when examined by gene expression analysis, have shown a profile that resembles only a minority of human breast cancer phenotypes, the basal-like type (Perou et al Nature 406: 747-752, 2000). A recent paper (Ayyakannu et al PNAS 103:3799-3804, 2006) employed pre-stasis HMEC (using the methods of Stampfer and Bartley, PNAS 1985) to readily obtain transformed HMEC after overexpression of the potentially oncogenic agent Wnt-1. The resulting lines had a gene expression profile resembling a different, distinct, minority human breast cancer phenotype, medullary carcinomas.

Figure 17:
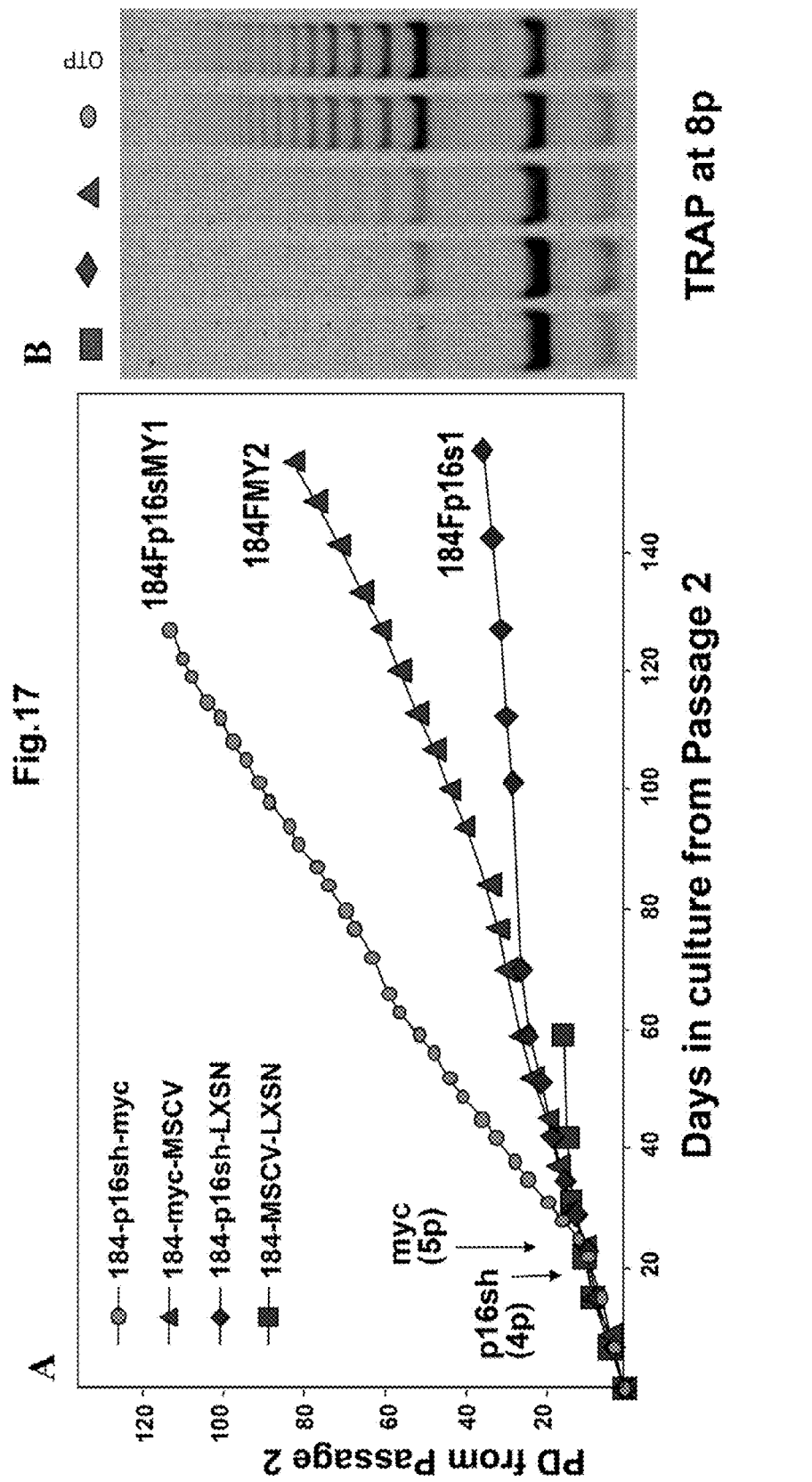
FIG. 17 shows transduction of pre-stasis 184 HMEC, batch F, with c-myc and/or p16shRNA: (A) A graph showing cumulative PD; 184F HMEC were started in MM in primary culture and switched to M85 at passage 2. (B) A photograph of a gel for an assay of telomerase activity at passage 8 showing the upregulation of activity in transduced cells.

Preliminary studies have examined the effects of the c-myc oncogene on telomerase expression and growth potential in different pre-stasis and post-stasis HMEC populations (FIG. 17), although systematic comparison of cells grown in the same medium has not yet been done. Pre-stasis 184 HMEC grown in M85 from passage 2 were retrovirally infected at 4p with a p16 small interfering RNA (p16sh) or empty vector (MSCV) and selected with puromycin. At 5p the 184-MSCV and 184-p16sh cells were infected with c-myc or empty vector (LXSN) followed by G418 selection. Cumulative PD levels were calculated (FIG. 17A) and telomerase activity assayed at 8p (FIG. 17B). The control 184-MSCV-LXSN cells ceased growth by 10p; 184-p16sh-LXSN cells grew well to 12p, after which their growth rate slowed. In contrast, the 184-myc-MSCV cultures initially showed a mixture of larger flat and smaller highly mitotic cells, but by15p the smaller cells predominated and the population has maintained rapid growth. The 184-p16sh-myc cells grew well and the population has maintained indefinite growth. These immortal populations have not yet been examined to determine whether they are derived from a few cells or represent widespread immortal transformation of the pre-stasis population. In contrast, in ten separate experiments, only one presumably clonal immortal outgrowth in c-myc transduced post selection HMEC was seen.

At 8p the vector control showed little or no detectable telomerase activity and the 184-p16sh-LXSN low activity. Significantly increased telomerase activity was seen in 184-myc-MSCV and the largest increase observed in the 184-p16sh-myc cells. In previous studies, we and others have seen low level telomerase activity in some MM-grown proliferating pre-stasis HMEC (Garbe, J. et al., Viral oncogenes accelerate conversion to immortality of cultured human mammary epithelial cells. Oncogene, 18: 2169-2180, 1999.; Belair, C. D. et al., Telomerase activity: a biomarker of cell proliferation, not malignant transformation. Proc. Natl. Acad. Sci. USA, 94: 13677-13682, 1998.) under conditions where no activity was seen in post-selection HMEC. We also previously saw that c-myc transduction increased telomerase in MM-grown pre-stasis 48L HMEC but not in post-selection 184 HMEC (Garbe, J. et al., Oncogene, 18: 2169-2180).

Figure 16:
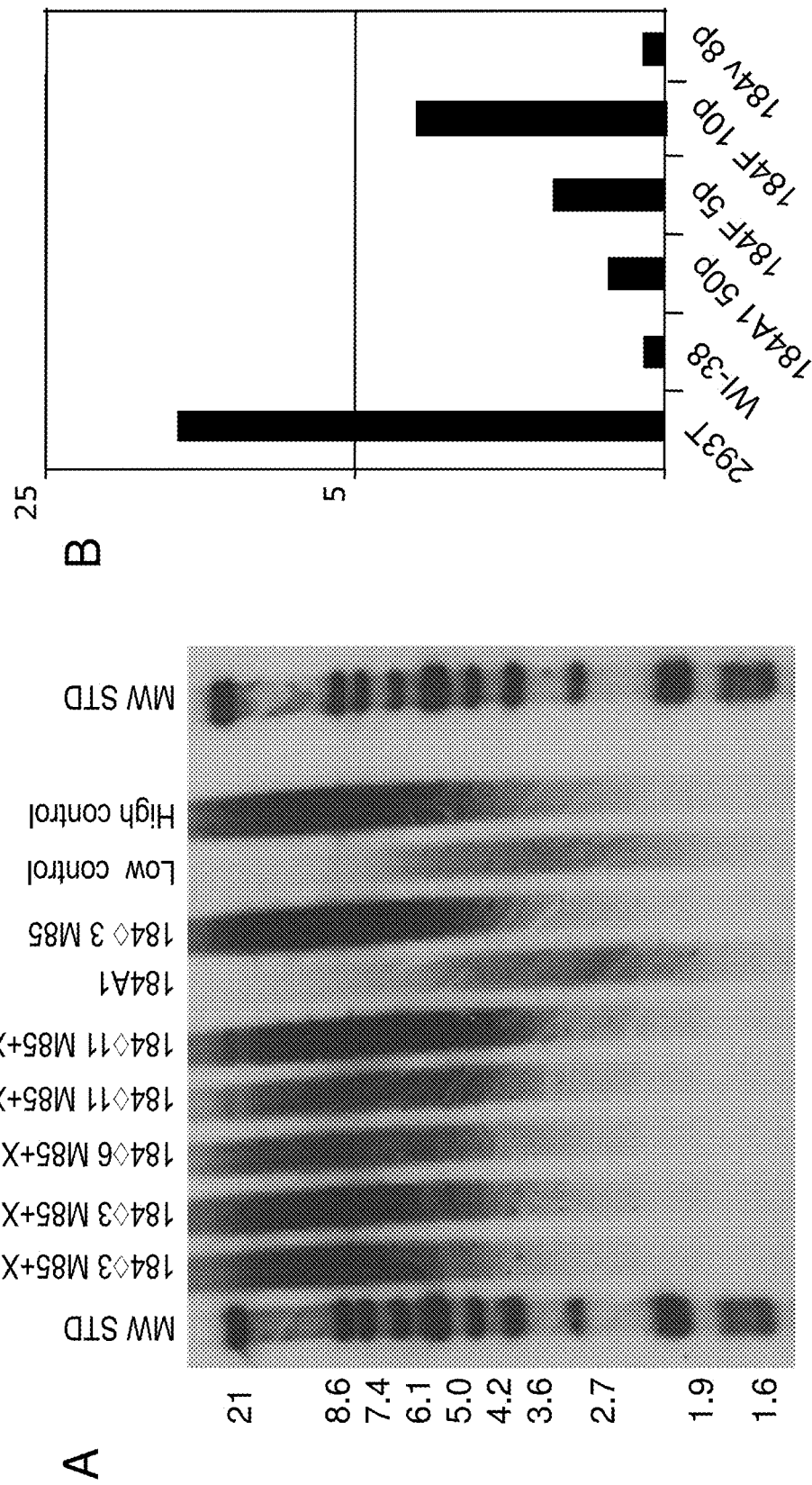
FIG. 16 showing telomere length and hTERT expression in pre-stasis 184 HMEC (A) shows a gel of the mean TRF length of pre-stasis 184◇ HMEC grown in M85±oxytocin (X). These data show a very slow reduction in mean TRF length as the 184◇ cultures are subcultured from passage 3 to passage 11, suggesting ongoing telomere maintenance with cell passage. (B) shows a graph of hTERT expression by RT-PCR of pre-stasis 184 HMEC batch F (primary culture was in MM) grown in M85 from passage 2. Pre-stasis 184F at passages 5 and 10 show significant hTERT expression compared to negative controls (WI-38 fibroblasts, post-selection 184v) as well as to the immortal line 184A1 with known TRAP activity.

FIG. 16 shows that pre-stasis 184 HMEC display some expression of hTERT, the catalytic subunit of telomerase, while showing very minimal loss of telomere length when subcultured from passage 3 to passage 11. These data indicate that pre-stasis HMEC, unlike the post-stasis post-selection HMEC, may express telomerase activity.

Figure 11:
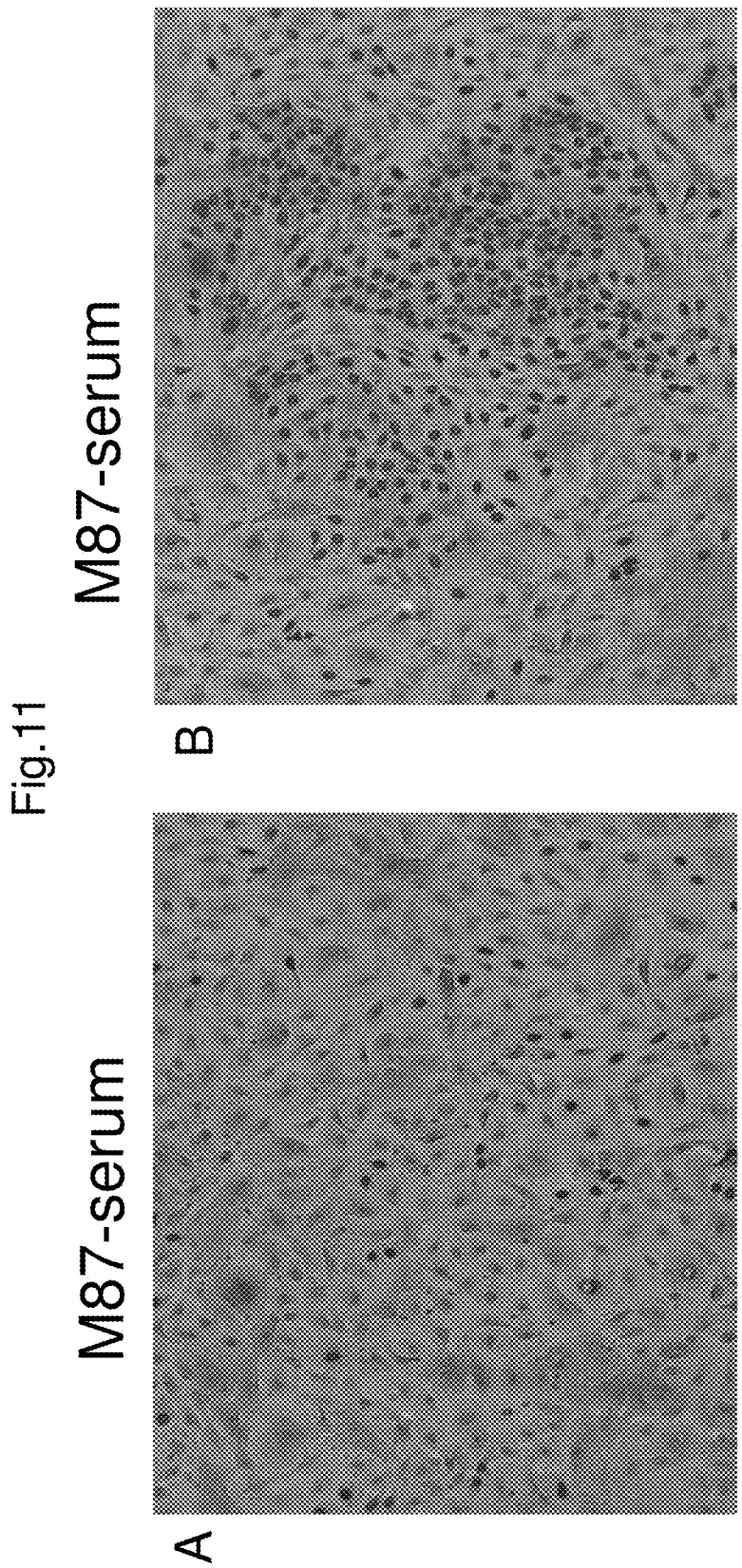
FIG. 11 shows (A & B) Photographs showing the requirement of pre-stasis HMEC 184, batch ◇, on EGF receptor (EGFR) stimulation for growth. Unlike the stringent dependence upon EGFR signal transduction for proliferation seen in finite post-stasis post-selection HMEC and non-malignant immortal HMEC lines, some pre-stasis HMEC can maintain growth (labeled nuclei) in medium minus EGF plus an antibody against the EGFR (MAb225). These data indicate the heterogeneity of this pre-stasis population with respect to dependence upon EGFR signaling for proliferation.

Altogether, these data support our hypothesis that pre-stasis HMEC may have less stringent repression of telomerase than cells that have encountered stasis, and that pre-stasis HMEC may be more vulnerable to transformation. Since it has been very difficult to generate transformed HMEC starting from normal tissues, use of un-stressed pre-stasis cells as targets for oncogenic transformation may allow for a greater ease of transformation. The presence of much more heterogeneity in the M85-grown pre-stasis HMEC (note keratin 19 positive cells in the pre-stasis population, FIG. 6, and EGFR independent cells in FIG. 11) may also result in a greater range of transformed cell types, including transformed cells with gene expression profiles that resemble the majority of human breast cancers. Such lines may be useful for understanding the mechanisms of breast cancer pathogenesis, as well as to study agents that might inhibit or reverse pathogenesis.

Example 3

Examining Mechanism of Oxytocin-induced Growth for Pre-stasis HMEC

Our initial studies will determine whether oxytocin is affecting telomerase activity (hTERT expression and TRAP activity), telomere length (mean TRF length) and expression of p16 and its regulators (e.g., ets transcription factors (see Yaswen, P. and Stampfer, M. R. Molecular changes accompanying senescence and immortalization of cultured human mammary epithelial cells. Int. J. Biochem. Cell Biol., 2002.)) in the best available medium. If oxytocin influences telomerase expression, additional studies will assay the effects of stresses on this function. Further studies, in collaboration with others, would look for downstream effects in the PI3K pathway, including on molecules associated with the cellular cytoskeleton (e.g., Rho GTPases) and cellular metabolism (e.g., mTOR pathway). Additional studies will compare gene expression profiles, and protein synthesis, in pre-stasis HMEC with and without exposure to oxytocin. Analysis of differences in gene expression profiles of pre-stasis HMEC from specimen 184 and 48R in media with and without oxytocin (FIG. 14) may suggest avenues to explore in determining the effect of oxytocin.

Established techniques can be used to measure mean TRF length and hTERT expression and activity. Suitable techniques are described in, for example, Stampfer, M. et al., Expression of the telomerase catalytic subunit, hTERT, induces resistance to transforming growth factor β growth inhibition in p16$^{INK4}$ (−) human mammary epithelial cells. Proc. Natl. Acad. Sci, USA., 98: 4498-4503, 2001., Garbe, J. et al., Viral oncogenes accelerate conversion to immortality of cultured human mammary epithelial cells. Oncogene, 18: 2169-2180, 1999., Stampfer, M. R. et al., Loss of p53 function accelerates acquisition of telomerase activity in indefinite lifespan human mammary epithelial cell lines. Oncogene, 22: 5238-5251, 2003., which are hereby incorporated by reference, can be used to measure mean TRF length and hTERT expression and activity.

Example 4

Characterization of Cell Populations

Short-term growth assays are done by measuring 24 hr labeling index (LI) at midconfluence and p16 expression and cell numbers at confluence in different media (as shown in FIG. 13). Long-term assays are done by placing cells in different media at early passages and determining total PD prior to stasis (as shown in FIGS. 8, 9). Other assays will transfer growing populations a few passages before stasis to media lacking specific components and assay LI and p16 (as shown in FIG. 12).

Cultures can be monitored for capacity to express p16, LI and DNA content when they cease proliferation, to ensure that the conditions do not result in the emergence of post-selection cells. In addition to the present description and the Examples, future studies should address determining culture conditions that can provide more in vivo like conditions of 3D architecture and polarity. It is recommended that established lab techniques are used to measure cell numbers, cumulative PD, LI, p16 expression and DNA content.

In the absence of stasis, cultured HMEC should proliferate with minimal p16 expression until they encounter the telomere-based barrier, agonescence (~70 total PD in HMEC from specimen 184, ~100 from specimen 48). Although this number of PD is not now achieved in cultured pre-stasis human epithelial cells, some cultured human fibroblasts such as the BJ strain can show >80 PD. It is proposed to start by culturing primary organoids from specimens 184, 48, and 240 in M85, and freezing down batches of second passage cells for future use.

Figure 6:
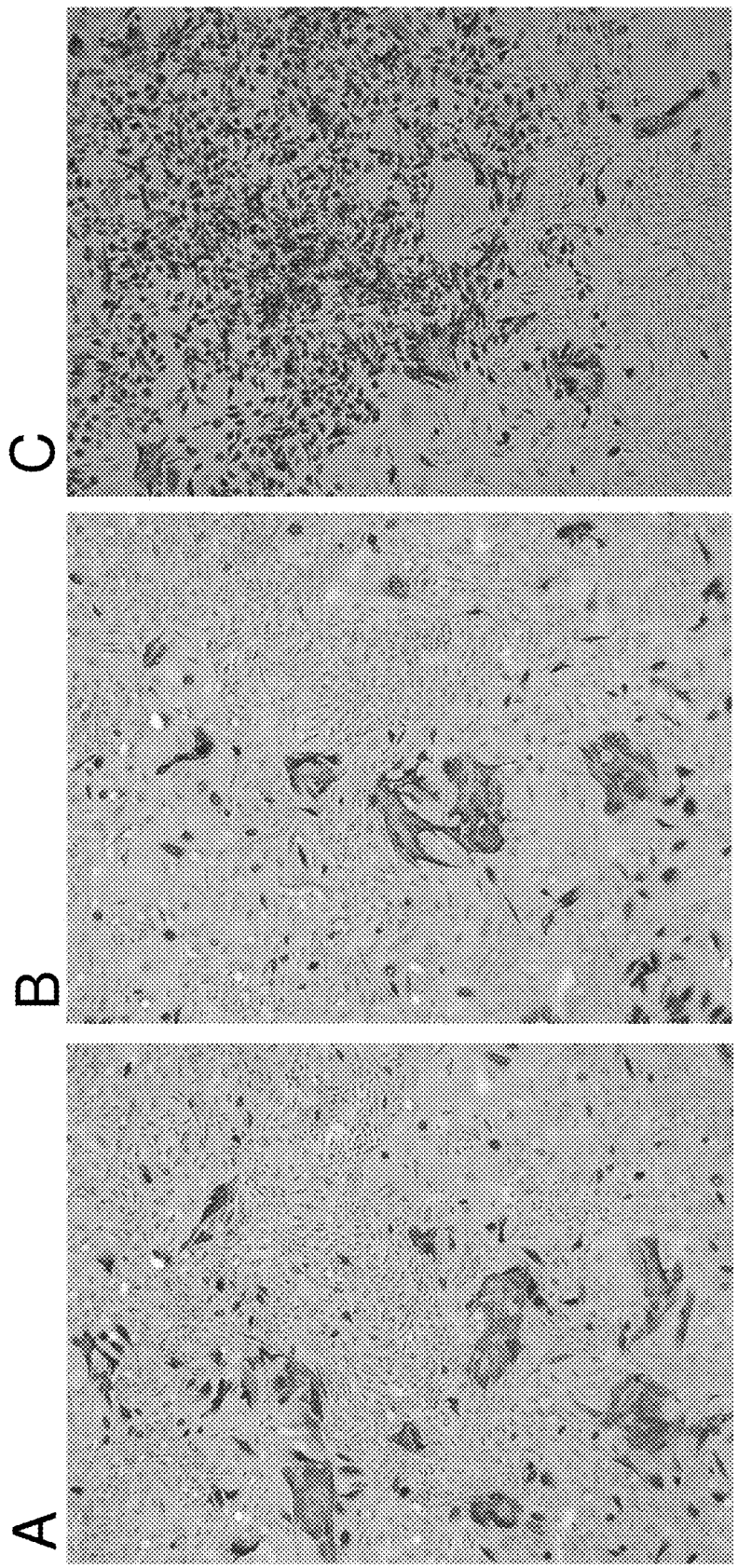
FIG. 6 is a set of (A, B, & C) photographs showing growth of pre-stasis 184 HMEC, batch ◇, in M85+oxytocin showing the presence of cells that express keratin 19, which has been associated with both a luminal and a stem cell phenotype. Prior culture conditions for growth of pre-stasis HMEC produced cells that showed a phenotype similar to basal HMEC in vivo (e.g., no expression of keratin 19 past primary culture). HMEC grown in M85 can express keratin 19 in proliferating cell populations at higher passages.

The use of pre-stasis HMEC will greatly benefit by information on cellular phenotypes and gene expression. As shown in FIG. 6, pre-stasis HMEC grown in M85 can express keratin 19, a marker of specific HMEC types that has previously been difficult to demonstrate in ongoing proliferative populations in culture. Keratin 19 is expressed by the majority of human breast cancers, but is not expressed in in vitro transformed cell lines derived from post-stasis HMEC. In particular, we want to assay for properties that can identify basal vs. luminal, or differentiated characteristics, e.g., keratins, mucins, α-actin, vimentin, estrogen receptors, EPHA2, integrin receptors, SCA1. Some assays will be performed using immunohistochemistry or immunofluorescence procedures established in the Stampfer laboratory and by collaborators (Stampfer, M. et al., Expression of the telomerase catalytic subunit, hTERT, induces resistance to transforming growth factor β growth inhibition in p16$^{INK4}$(−) human mammary epithelial cells. Proc. Natl. Acad. Sci, USA, 98: 4498-4503, 2001.; Romanov, S. et al. Normal human mammary epithelial cells spontaneously escape senescence and acquire genomic changes. Nature, 409: 633-637, 2001.). Experiments for examination of gene expression by microarrays using Affymetrix Hu133A Gene Chip arrays, containing probes for ~18,400 transcripts including 14,500 well annotated genes were performed.

Referring now to FIG. 14, gene expression data of the indicated HMEC at different passage levels were organized using unsupervised hierarchical clustering restricted to probe sets that varied by more than Log 2 2.0. The gene trees are not shown. HMEC cultures examined are: pre-stasis 184◇ grown±oxytocin and 48RT−oxytocin, from passage 2 until stasis; post-stasis post-selection 184 batch v and 48R batch S when actively growing (184v 9p, 48RT 11p) and at agonescence (184v 14p, 48RT 22p). FIG. 14(A) shows unsupervised clustering of growing and senescent (stasis or agonescence) HMEC from specimens 184 and 48R showing a partial probe set. The analysis baseline was calculated from the average of all samples; 891 probe sets were used for the clustering. Of note is the clear distinctions in pre-stasis cells between growing cultures and those at stasis; some differences between growing pre-stasis and post-selection HMEC; some differences between cells at stasis vs. agonescence; some differences between growing post-selection and agonescence; some differences between individuals. FIG. 14(B) shows unsupervised clustering of senescent (stasis or agonescence) HMEC from specimens 184 and 48R showing a partial probe set; 529 probe sets were used for the clustering. These unsupervised clusterings support our model of the distinct senescence barriers, showing that gene expression at stasis is distinct from that seen at agonescence. The data also show differences in expression between growing populations and those at the senescence barriers, and differences between individual specimens 184◇ and 48RT.

Figure 15:
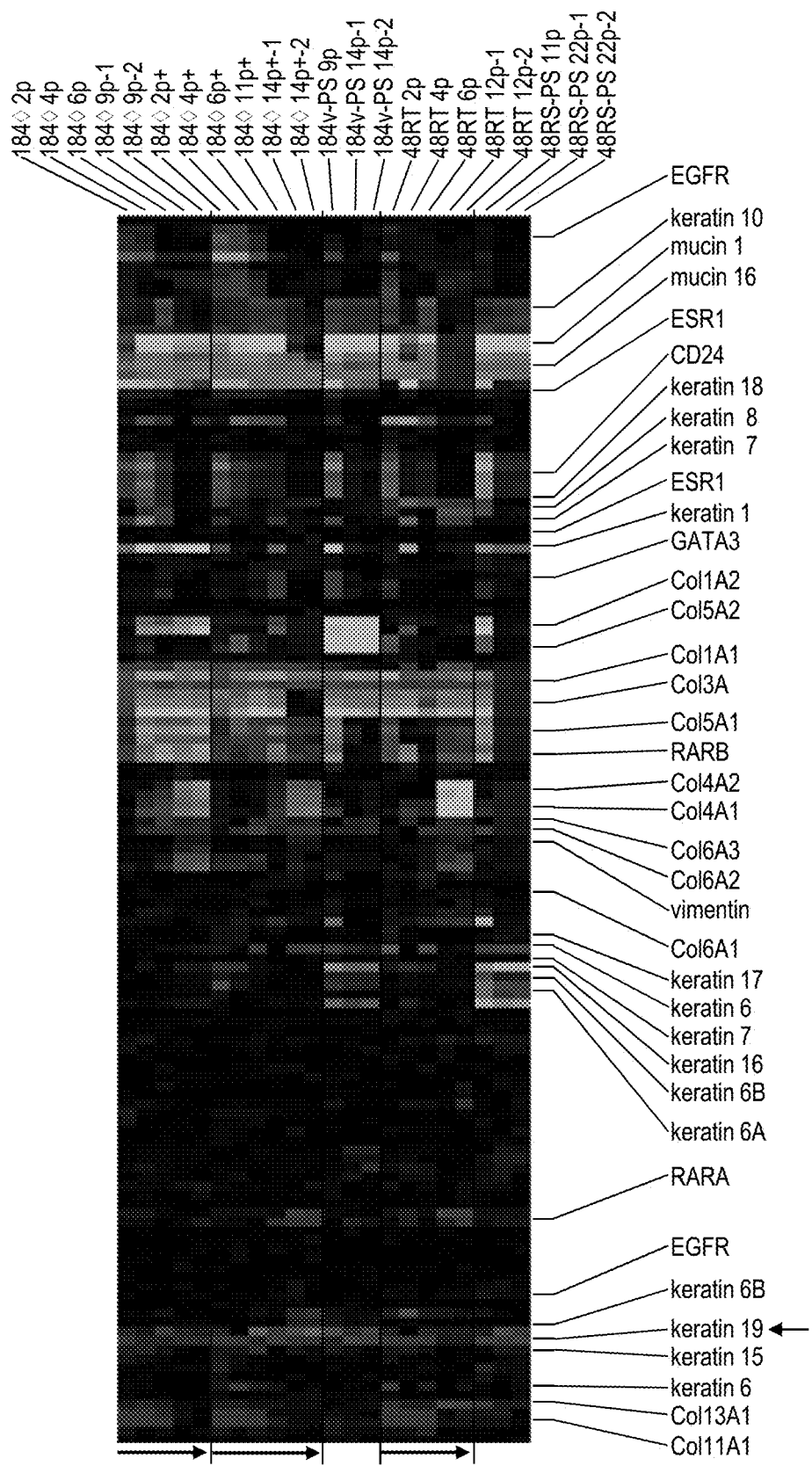
FIG. 15 is a heat map showing supervised clustering of selected gene expression in growing and senescent (stasis or agonescence) pre-stasis and post-selection HMEC.

FIG. 15 is a heat map showing supervised clustering of selected gene expression in growing and senescent (stasis or agonescence) pre-stasis and post-selection HMEC. Expression level of genes associated with keratins, extracellular matrix, and basal or luminal phenotypes were selected, and some of them identified in the figure. Gene expression data was organized according to specimen and passage level, separating pre-stasis from post-selection populations. Arrows at the left indicate increasing passage number. Some of the selected genes are listed on the bottom. Note the continued expression of K19 in 48RT, but not 184◇, through stasis. Other differences can be noted between individuals 184 and 48R.

Further, an examination of telomere associated properties, i.e. mean TRF (telomere restriction fragment) length, hTERT expression and telomerase activity (FIG. 16), is being conducted. Additional assays will be performed using immunohistochemistry or immunofluorescence procedures using standard techniques as known in the art.

These studies should allow us to define culture conditions permissive for extensive growth of well-characterized pre-stasis HMEC, the cells likely most reflective of normal HMEC in vivo, compared to the commonly used post-selection HMEC. Such an achievement may have large repercussions on future investigation of normal and aberrant human breast biology. Possibly, the role of some factors that may significantly affect pre-stasis HMEC biology has been obscured because of their limited growth in vitro. We are seeing a dramatic effect of oxytocin (a factor whose synthesis in vivo is influenced by estrogens and which may act through the PI3K pathway in cells), and future studies will examine the mechanism of its action. Other possible factors whose effects on pre-stasis HMEC could be evaluated include hormones such as estrogens and progestins, environmental carcinogens, and oncogenes associated with human breast cancer.

HMEC which have experienced less stress in culture as seen by increased PD potential may have less stringent repression of telomerase and may be more vulnerable to c-myc-induced telomerase reactivation and immortalization (FIG. 17). These cultures may also be vulnerable to transformation via other agents that increase telomerase activity.

Example 5

Telomerase

One embodiment is an assay for hTERT expression by RT-PCR, telomerase activity by TRAP, and mean TRF (telomere) length as described (Stampfer, M. R. et al., Loss of p53 function accelerates acquisition of telomerase activity in indefinite lifespan human mammary epithelial cell lines. Oncogene, 22: 5238-5251, 2003.) in pre-stasis HMEC populations to determine possible correlation among culture conditions, differing PD potential and onset of stasis with telomerase activity and the rate of telomere erosion with ongoing proliferation.

Example 6

Aging and Carcinogenesis Assays

Further similar studies may enable development of assays to determine possible effects of factors that could influence aging and/or carcinogenesis. For example, the addition of the anti-stress factor oxytocin causes a significant increase in total PD. The effects of additional factors in increasing or decreasing total PD can be measured using standardized pre-stasis cell batches. Other assays such as seen in FIGS. 9, 12, and 13 that measure growth and p16 expression following removal of specific factors can also be employed. Overcoming stasis is considered an important step in the carcinogenesis pathway.

Referring now to FIG. 12(A), cells were started as primary organoids in MM and switched at passage 3 (experiment 1) or at passage 2 (experiment 2) to M85 in 3% 02. In experiment 2, some cells were switched back to MM in 3% 02 at subculture from passage 5 to passage 6. Note the lower level of p16 expression and different cell morphology in HMEC cultured in M85 at 8p vs. at stasis arrest at 11p, and the rapid cessation of growth and increase in p16 expression when cells were transferred to MM at passage 6. Post-selection 184 HMEC are shown as a negative control for p16. These data suggest that pre-stasis HMEC grown in M85-based media that are close to stasis may be quickly propelled into stasis by switching to MM.

Referring now to FIG. 13, pre-stasis HMEC grown in M85+oxytocin, 48RT and 240LB, were switched to the indicated media at passage 5, subcultured to passage 6, and then assayed when midconfluent for LI and p16 expression. Note the reciprocity of LI and p16 (together ~100%). In this situation, starting with pre-stasis HMEC that were still many passages away from stasis, switching to media that support fewer pre-stasis PD (i.e., MM or MCDB170) caused only moderate decreases in proliferative potential over the time frame examined.

Almost all human carcinomas contain an error that would allow stasis to be overcome (e.g., loss of Rb function, loss of p16 expression, and changes in other factors that influence Rb activity). Although a spontaneous selection process (overcoming of stasis) has not been observed in HMEC grown in MM or M85, exposure to a chemical carcinogen was able to enable pre-stasis HMEC grown in MM to overcome stasis, associated with loss of p16 expression (Stampfer, M. R. and Bartley, J. C., Induction of transformation and continuous cell lines from normal human mammary epithelial cells after exposure to benzo(a)pyrene. *Proc Natl Acad Sci* (USA) 82:2394-2398, 1985, Brenner & Aldaz, Chromosome 9p allelic loss and p16/CDKN2 in breast cancer and evidence of p16 inactivation in immortal breast epithelial cells, *Cancer Research* 55: 2892-2895, 1995). Additionally, growth in the high-stress serum free medium MCDB170 enabled rare cells to silence p16 expression and overcome stasis (Hammand et al, 1984), as did inactivation of the tumor suppressor p53 (Garbe et al, in preparation [data not shown]). An assay, using large standardized pre-stasis cell batches, to measure whether a factor can induce pre-stasis HMEC to overcome stasis, may indicate potential carcinogenic agents. The absence of a spontaneous process to overcome stasis in M85 facilitates such an assay. Further, standardized pre-stasis populations could be used to assay potential carcinogenic agents ability to overcome OIS in response to overexpressed oncogenes such as Raf-1 or Ras, since we have shown that untreated pre-stasis and post-selection HMEC show rapid loss of proliferative potential when challenged with overexpressed Raf-1 (Olsen C. L. et al., Raf-1-induced growth arrest in human mammary epithelial cells is p16-independent and is overcome in immortal cells during conversion, Oncogene 21:6328-6339, 2002).

Example 7

Generation of Assays on the Effects of Pro-/Anti-carcinogenic Agents

The long-term growth potential of pre-stasis HMEC in M85+oxytocin allows the generation of large standardized cell batches which can be reproducible starting points for assays on the effects of pro- or anti-carcinogenic agents. These populations can be challenged with potential carcinogenic agents and assayed for their ability to subsequently overcome stasis or OIS. The absence of spontaneous selection to overcome stasis in the M85 media facilitates such assays. Conversely, the presence of rare colonies that can escape stasis after exposure to potentially oncogenic agents (e.g., BaP, overexpressed c-myc, inactivation of p53, high stress medium) suggests that potential oncogenic agents may induce pre-stasis HMEC to overcome stasis. Quantitative assays may be designed wherein HMEC exposed to agents in M85+oxytocin are then switched to a media that induces rapid stasis (as in FIG. 12) and then observed for the appearance and number of colonies induced to escape stasis. Alternatively, pre-stasis HMEC may be transduced with oncogenes whose expression is dependent upon an inducer (e.g., Raf:ER as described in Olsen et al., 2002), exposed to potential oncogenic agents, and the oncogene induced. Untreated cells would be expected to rapidly lose proliferative potential (Olsen et al., 2002). Treated cultures can be observed for the appearance and number of colonies induced to escape OIS.

Example 8

Generation of New Cell Lines

Transduction of unstressed pre-stasis cells grown in M85 gave rise to immortal cell lines with significantly increased frequency of immortal transformation compared to the extreme difficulty in obtaining immortal transformation of post-stasis post-selection HMEC using pathologically related agents. As shown in FIG. 17, transduction of unstressed pre-stasis HMEC grown in M85 gave rise to immortal cell lines in all conditions except the control. Cultures were transduced with p16shRNA or vector control at passage 4, and c-myc or vector control at passage 5. Note that transduction of these unstressed pre-stasis HMEC grown in M85 gave rise to immortal cell lines in all conditions except the control. This frequency of immortal transformation contrasts with the extreme difficulty in obtaining immortal transformation of post-stasis post-selection HMEC, and suggests that genetic manipulations using unstressed pre-stasis HMEC may be a preferable route for immortal transformation of human epithelial cells. It well may be that the more heterogeneous population of cells grown in M85 may be more susceptible to oncogenic transformation and may produce a greater range of phenotypes in the transformed cells. Thus in one embodiment, a method is provided for generation of a greater number and greater range of lines, with greater number of phenotypes.

Such new lines may better reflect the variety of phenotypes seen in breast cancer derived cells, and thereby provide experimentally tractable systems to determine the pathway by which different oncogenic insults may transform normal HMEC, as well as to assess the potential of therapeutic or other agents to prevent this transformation.

While the present media formulations, compositions, methods and processes have been described with reference to specific details of certain exemplary embodiments thereof, it is not intended that such details be regarded as limitations upon the scope of the invention. The present examples, methods, procedures, specific compounds and media are meant to exemplify and illustrate the invention and should in no way be seen as limiting the scope of the invention. Any patents, references and publications, mentioned above and below in this specification are indicative of levels of those skilled in the art to which the invention pertains and are hereby incorporated by reference to the same extent as if each was specifically and individually incorporated by reference.

What is claimed is:

1. A method of increasing population doublings in a cell culture of human epithelial cells with finite life span, comprising the steps of:
    providing a cell culture of pre-stasis human epithelial cells, and
    providing a cell culture medium comprising a mixture of
    (a) 30% to 60% of MM medium with up to 3% serum and (b) 40% to 70% of a different, serum-free medium comprising defined ingredients for growth of human mammary epithelial cells, further comprising (c) an effective amount of an anti-stress associated compound, whereby population doublings and finite life span of said cell culture are increased as compared to a control containing only either the MM medium with serum or a serum free medium.

2. The method of claim 1, wherein the medium with serum further contains conditioned media.

3. The method of claim 1, wherein the medium with serum does not contain conditioned media.

4. The method of claim 1, wherein the serum-free medium is MCDB170.

5. The method of claim 1, wherein the cell culture medium further comprises at least one of EGF, hydrocortisone, bovine pituitary extract, estradiol, triiodothyronine, insulin or insulin-like growth factor, or lipid rich bovine serum albumin (BSA).

6. The method of claim 1, wherein the human epithelial cells are human mammary epithelial cells.

7. The method of claim 1 wherein the cell culture comprises 50% medium with serum and 50% serum-free medium.

8. The method of claim 1 wherein the cell culture comprises 30% medium with serum and 70% serum-free medium.

9. The method of claim 1 wherein the cell culture comprises 60% medium with serum and 40% serum-free medium.

10. The method of claim 1, wherein the anti-stress associated compound is selected from the group consisting of oxytocin, lipid rich bovine serum albumin (BSA), angiotensin II, serotonin (5-HT), melanin concentrating hormone, histamine, bombesin and gastrin-releasing peptide (GRP), glucagons-like peptide-1 (GLP-1), cholecystokinin (CCK), dopamine, and corticotrophin releasing factor.

11. The method of claim 10, wherein the anti-stress associated compound is oxytocin.

12. The method of claim 11, wherein the effective amount of oxytocin is a concentration between 0.05 nM and 5.0 nM.

13. The method of claim 11, wherein the effective amount of oxytocin is a concentration of 0.1 nM.

14. The method of claim 11 further comprising the step of providing a second anti-stress associated compound selected from the group consisting of lipid rich bovine serum albumin (BSA), angiotensin II, serotonin (5-HT), melanin concentrating hormone, histamine, bombesin and gastrin-releasing peptide (GRP), glucagons-like peptide-1 (GLP-1), cholecystokinin (CCK), dopamine, and corticotrophin releasing factor.

15. The method of claim 14, wherein the second anti-stress associated compound is lipid rich bovine serum albumin (BSA).

16. The method of claim 10, wherein the anti-stress associated compound is added to the primary passage of the cell culture.

17. The method of claim 10, wherein the anti-stress associated compound is added at or after the second passage of the cell culture.

18. The method of claim 1 further comprising a step of growing the cell culture on an extracellular matrix material.

19. The method of claim 18 wherein the extracellular matrix is laminin.

20. The method of claim 1 further wherein said cell culture is cultured for at least 30 population doublings.

* * * * *